(12) United States Patent
Gregerson et al.

(10) Patent No.: US 10,987,068 B2
(45) Date of Patent: *Apr. 27, 2021

(54) MULTI-DIRECTIONAL X-RAY IMAGING SYSTEM

(71) Applicant: MOBIUS IMAGING, LLC, Shirley, MA (US)

(72) Inventors: Eugene A. Gregerson, Bolton, MA (US); Russell Stanton, Lunenberg, MA (US); Michael Connor, Dunstable, MA (US); Michael Allen, Boxborough, MA (US); Paul Sebring, Townsend, MA (US); Robert Powell, Bolton, MA (US)

(73) Assignee: Mobius Imaging LLC, Shirley, MA (US)

( * ) Notice: Subject to any disclaimer, the term of this patent is extended or adjusted under 35 U.S.C. 154(b) by 273 days.

This patent is subject to a terminal disclaimer.

(21) Appl. No.: 15/972,964

(22) Filed: May 7, 2018

(65) Prior Publication Data

US 2018/0353143 A1 Dec. 13, 2018

Related U.S. Application Data

(63) Continuation-in-part of application No. 15/359,997, filed on Nov. 23, 2016, now Pat. No. 9,962,132, (Continued)

(51) Int. Cl.
*A61B 6/03* (2006.01)
*A61B 6/02* (2006.01)
(Continued)

(52) U.S. Cl.
CPC ............ *A61B 6/027* (2013.01); *A61B 6/032* (2013.01); *A61B 6/035* (2013.01); *A61B 6/04* (2013.01);
(Continued)

(58) Field of Classification Search
CPC .......... A61B 6/032; A61B 6/035; A61B 6/04; A61B 6/0407; A61B 6/44; A61B 6/4405; A61B 6/4417
See application file for complete search history.

(56) References Cited

U.S. PATENT DOCUMENTS 4,928,283 A 5/1990 Gordon
4,961,208 A 10/1990 Okada
(Continued)

FOREIGN PATENT DOCUMENTS

DE 19846980 A1 10/1999
EP 0067933 A1 12/1982
(Continued)

OTHER PUBLICATIONS

U.S. Appl. No. 61/658,650, filed Jun. 12, 2012.
(Continued)

*Primary Examiner* — Don K Wong
(74) *Attorney, Agent, or Firm* — Howard & Howard Attorneys PLLC

(57) ABSTRACT

An imaging system and methods including a gantry defining a bore and an imaging axis extending through the bore, and at least one support member that supports the gantry such that the imaging axis has a generally vertical orientation, where the gantry is displaceable with respect to the at least one support member in a generally vertical direction. The imaging system may be configured to obtain a vertical imaging scan (e.g., a helical x-ray CT scan), of a patient in a weight-bearing position. The gantry may be rotatable between a first position, in which the gantry is supported such that the imaging axis has a generally vertical orientation, and a second position, such that the imaging axis has a generally horizontal orientation. The gantry may be displaceable in a horizontal direction and the system may
(Continued)

perform a horizontal scan of a patient or object positioned within the bore.

12 Claims, 29 Drawing Sheets

Related U.S. Application Data which is a continuation-in-part of application No. 13/916,869, filed on Jun. 13, 2013, now Pat. No. 10,151,810.

(60) Provisional application No. 61/659,609, filed on Jun. 14, 2012.

(51) Int. Cl.
*A61B 6/00* (2006.01)
*A61B 6/04* (2006.01)

(52) U.S. Cl.
CPC .......... *A61B 6/4447* (2013.01); *A61B 6/4452* (2013.01); *A61B 6/504* (2013.01); *A61B 6/508* (2013.01)

(56) References Cited

U.S. PATENT DOCUMENTS

| | | |
|---|---|---|
| 5,448,607 A | 9/1995 | McKenna |
| 5,574,763 A | 11/1996 | Dehner |
| 5,574,769 A | 11/1996 | Dehner |
| 5,740,222 A | 4/1998 | Fujita et al. |
| 5,912,943 A * | 6/1999 | Deucher ............... H05G 1/02 378/167 |
| 6,102,567 A | 8/2000 | Cabral et al. |
| 6,104,775 A | 8/2000 | Tuy |
| 6,212,251 B1 | 4/2001 | Tomura et al. |
| 6,246,239 B1 | 6/2001 | Krogmann et al. |
| 6,426,989 B2 | 7/2002 | Grass et al. |
| 6,490,333 B1 | 12/2002 | Hsieh |
| 6,735,274 B1 | 5/2004 | Zahavi et al. |
| 6,794,871 B2 | 9/2004 | Imai et al. |
| 6,988,827 B2 | 1/2006 | Mueller |
| 6,996,204 B2 | 2/2006 | Grass et al. |
| 7,001,045 B2 | 2/2006 | Gregerson et al. |
| 7,175,347 B2 | 2/2007 | Tybinkowski et al. |
| 7,215,805 B2 | 5/2007 | Bruder et al. |
| 7,224,764 B2 | 5/2007 | Sukovic et al. |
| 7,388,941 B2 | 6/2008 | Sukovic et al. |
| 7,394,888 B2 | 7/2008 | Sukovic et al. |
| 7,397,895 B2 | 7/2008 | Bailey et al. |
| 7,456,407 B2 | 11/2008 | Stark |
| 7,568,836 B2 | 8/2009 | Bailey et al. |
| 7,607,832 B2 | 10/2009 | Jensen et al. |
| 7,637,660 B2 | 12/2009 | Tybinkowski et al. |
| 7,796,730 B2 | 9/2010 | Marash et al. |
| 7,806,589 B2 | 10/2010 | Tashman et al. |
| 7,944,208 B2 | 5/2011 | Dutto et al. |
| 7,963,696 B2 | 6/2011 | Bailey et al. |
| 8,118,488 B2 | 2/2012 | Gregerson |
| 8,251,584 B2 | 8/2012 | Tybinkowski et al. |
| 8,705,695 B2 | 4/2014 | Jabri et al. |
| 8,737,708 B2 | 5/2014 | Hartmann et al. |
| 8,746,973 B2 | 6/2014 | Gregerson et al. |
| 8,753,009 B2 | 6/2014 | Gregerson et al. |
| 8,770,839 B2 | 7/2014 | Gregerson et al. |
| 8,888,364 B2 | 11/2014 | Bailey et al. |
| 9,016,941 B2 | 4/2015 | Tybinkowski et al. |
| 9,398,886 B2 | 7/2016 | Gregerson et al. |
| 9,700,272 B2 | 7/2017 | Gregerson |
| 9,737,273 B2 | 8/2017 | Gregerson et al. |
| 9,795,022 B2 | 10/2017 | Duhamel |
| 9,820,704 B2 | 11/2017 | Tybinkowski et al. |
| 9,962,132 B2 | 5/2018 | Gregerson et al. |
| 10,151,810 B2 | 12/2018 | Gregerson et al. |
| 10,178,981 B2 | 1/2019 | Bailey et al. |
| 2005/0053186 A1 | 3/2005 | Sukovic et al. |
| 2005/0135560 A1 | 6/2005 | Dafni et al. |
| 2008/0123819 A1 | 5/2008 | Jensen et al. |
| 2009/0289663 A1 | 11/2009 | Sogomonyan et al. |
| 2010/0172468 A1 | 7/2010 | Gregerson |
| 2011/0228901 A1 | 9/2011 | Yorkston et al. |
| 2011/0228910 A1 | 9/2011 | Gregerson et al. |
| 2012/0189094 A1 * | 7/2012 | Neushul ............... A61B 6/4266 378/19 |
| 2012/0324648 A1 | 12/2012 | Amano |
| 2014/0139215 A1 | 5/2014 | Gregerson et al. |
| 2016/0338656 A1 | 11/2016 | Gregerson |
| 2017/0000451 A1 | 1/2017 | Aspelund et al. |
| 2017/0007334 A1 | 1/2017 | Crawford et al. |
| 2017/0071560 A1 | 3/2017 | Gregerson et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2018/0125439 A1 | 5/2018 | Nabeta et al. |
| 2018/0125440 A1 | 5/2018 | Gregerson |
| 2018/0177473 A1 | 6/2018 | Gregerson et al. |
| 2018/0214098 A1 | 8/2018 | Tybinkowski et al. |

FOREIGN PATENT DOCUMENTS

| | | |
|---|---|---|
| EP | 0495137 A1 | 7/1992 |
| JP | 02-123211 U | 10/1990 |
| JP | 04-352948 A | 12/1992 |
| JP | 2000-214263 A | 8/2000 |
| JP | 2000-312674 A | 11/2000 |
| JP | 2001-37747 A | 2/2001 |
| JP | 2008-278902 A | 11/2008 |
| WO | 2007-141221 A1 | 12/2007 |
| WO | 2011-111119 A1 | 9/2011 |
| WO | 2011-135191 A1 | 11/2011 |

OTHER PUBLICATIONS

International Search Report and Written Opinion issued in PCT Application No. PCT/US2013/045563 dated Sep. 16, 2013, 14 pages.
International Preliminary Report on Patentability (Chapter 1 of the Patent Cooperation Treaty) in International Application No. PCT/US2013/045563 dated Dec. 24, 2014, 11 pages.
European Office Communication and Supplementary European Search Report from the Munich Patent Office for Application No. 13804681.8-1660/2861148 in International Application No. PCT/US2013/045563 dated Dec. 17, 2015, 8 pages.
First Office Action from the European Patent Office in Application No. 13 804 681.8-1124 based on related Application No. PCT/US2013/045563, dated Jan. 9, 2018, 6 pages.

* cited by examiner

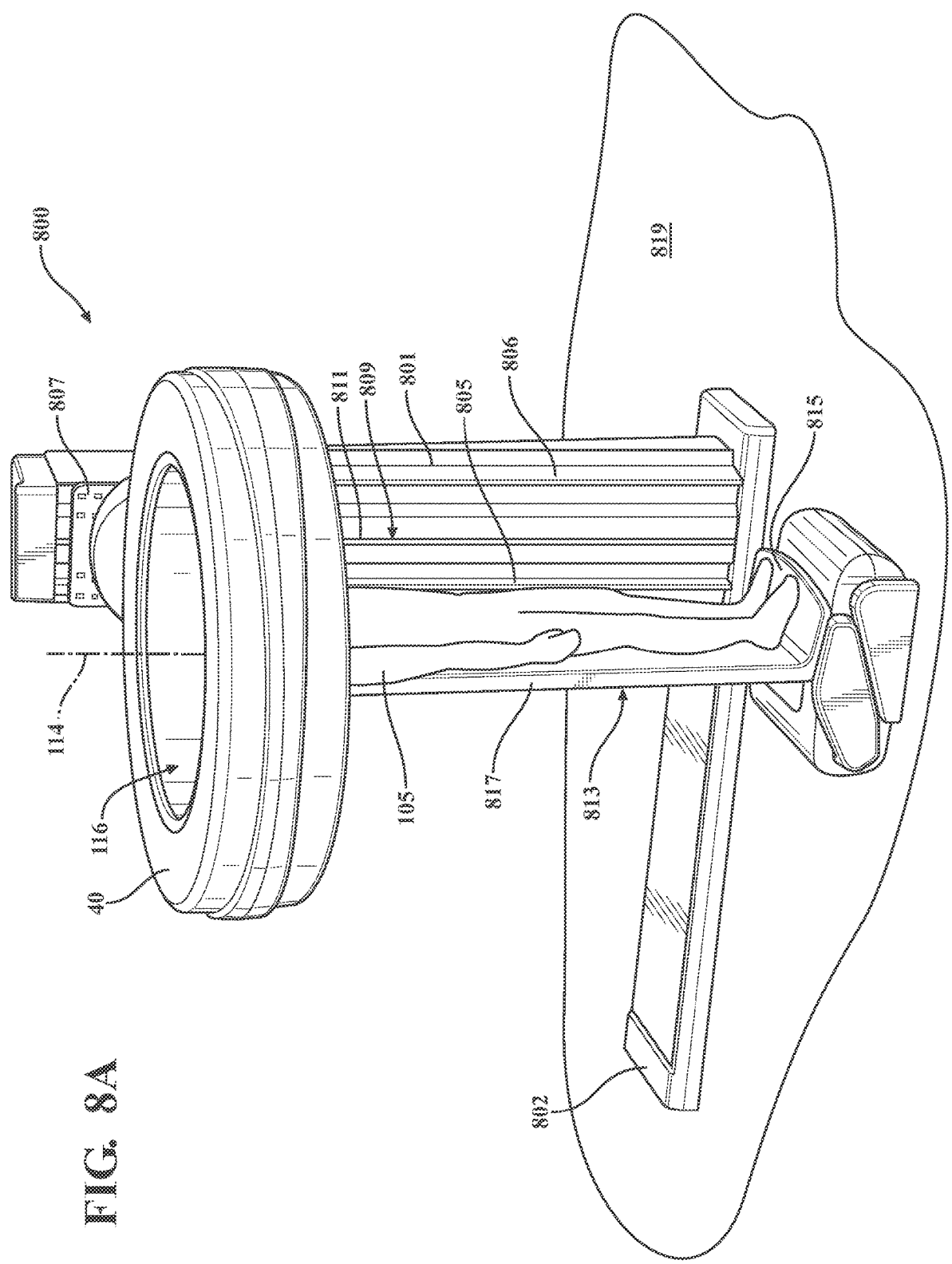

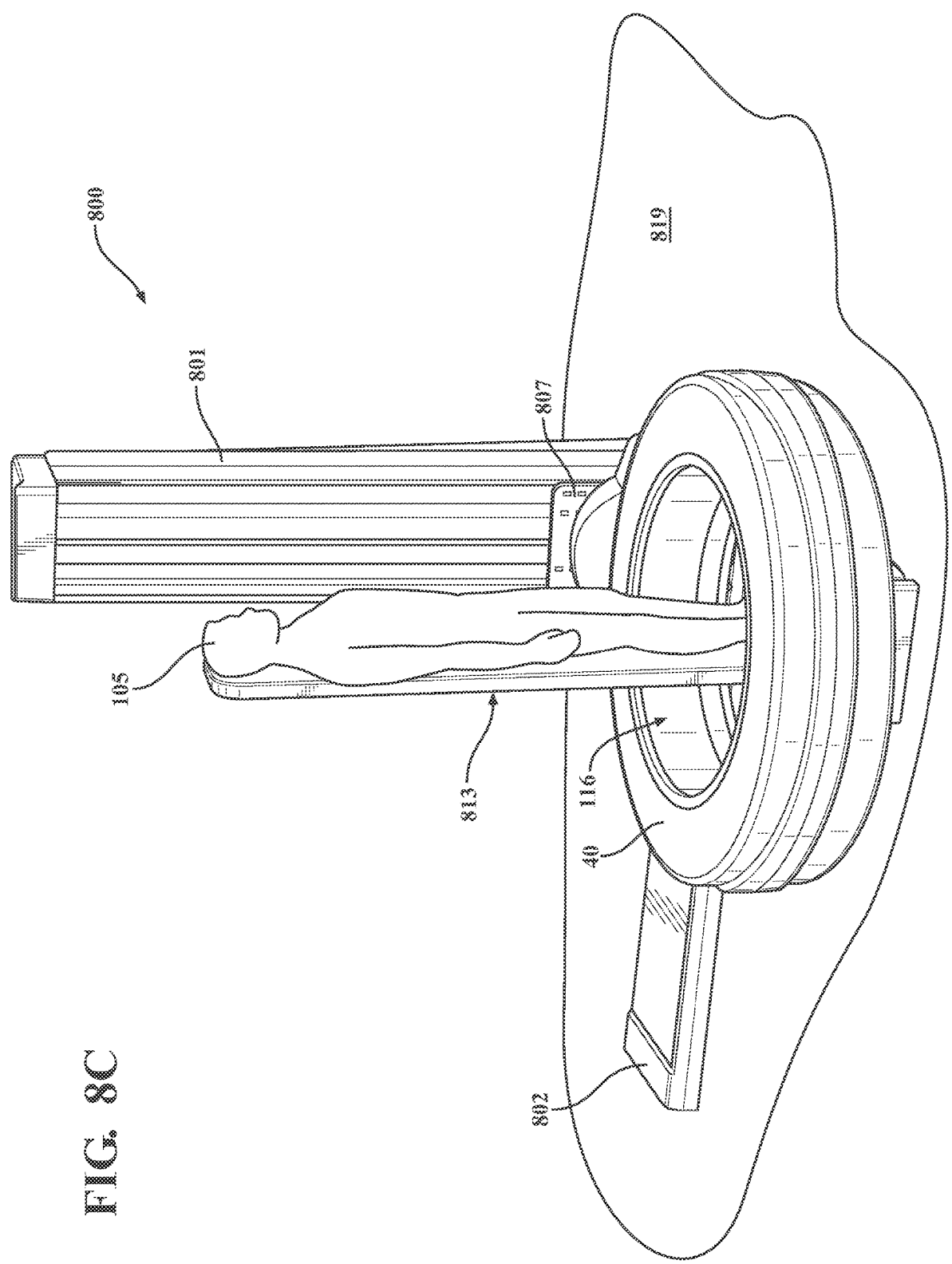

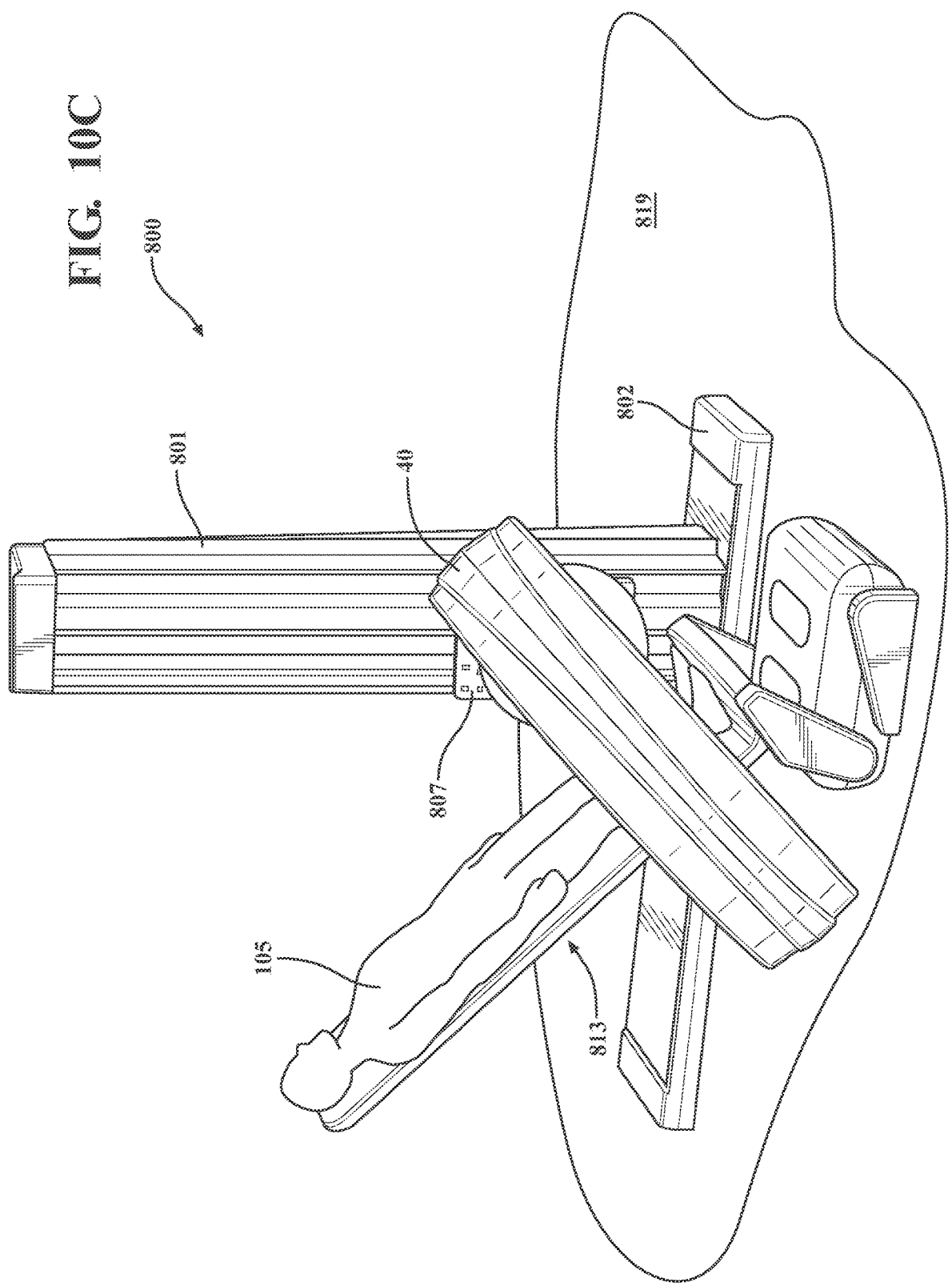

MULTI-DIRECTIONAL X-RAY IMAGING SYSTEM

RELATED APPLICATIONS

This application is a continuation-in-part of U.S. application Ser. No. 15/359,997, filed on Nov. 23, 2016, which is a continuation-in-part of U.S. application Ser. No. 13/916,869, filed on Jun. 13, 2013, which claims the benefit of priority to U.S. Provisional Application No. 61/659,609 filed on Jun. 14, 2012, the entire contents of which are incorporated herein by reference.

BACKGROUND

Conventional medical imaging devices, such as computed tomography (CT) and magnetic resonance (MR) imaging devices, are typically large, fixed bore devices. The patient must enter the device from the front or rear of the device in a lying position. These devices are limited in the types of imaging operations that may be performed.

SUMMARY

Embodiments include an imaging system having a gantry defining a central imaging bore and an imaging axis extending through the bore, the gantry comprising at least one imaging component for obtaining images of an object located within the bore, and at least one support member that supports the gantry such that the imaging axis has a generally vertical orientation, where the gantry is displaceable with respect to the at least one support member in a generally vertical direction.

In various embodiments, the gantry comprises a generally O-shaped housing having an internal cavity, and the imaging component(s), such as an x-ray source and/or x-ray detector, are rotatable around the gantry within the internal cavity. The imaging system may be configured to obtain a vertical imaging scan, such as a helical x-ray CT scan, of a patient in a weight bearing standing position.

In various embodiments, the gantry of the imaging system is rotatable with respect to the at least one support member between a first position, in which the gantry is supported such that the imaging axis has a generally vertical orientation, and a second position, in which the gantry is supported such that the imaging axis has a generally horizontal orientation. The gantry and the at least one support member may be displaceable in a generally horizontal direction relative to an object positioned within the bore. The system may thus perform a horizontal scan of a patient or object positioned within the bore.

In various embodiments, the gantry may be rotatable with respect to the at least one support member to a desired angle with respect to a tilted axis (i.e., an axis that is neither horizontal nor vertical). The gantry may be displaced both vertically and horizontally to perform an imaging scan along the titled axis. The angle of the gantry with respect to the tilted axis may remain fixed during the scan.

In further embodiments, a method of imaging an object includes positioning an object within a central imaging bore of a gantry comprising at least one imaging component for obtaining images of the object, the gantry having an imaging axis extending through the bore in a generally vertical orientation, displacing the gantry in a generally vertical direction with respect to the object, and obtaining image data of the object using the at least one imaging component.

In various embodiments, the method may further include rotating the gantry from a generally vertical orientation to a generally horizontal orientation, and displacing the gantry in a relatively horizontal direction relative to the object to perform an imaging scan. In various embodiments, the method may further include rotating the gantry to an angle with respect to a tilted axis, and displacing the gantry in both horizontal and vertical directions to perform an imaging scan along the tilted axis.

Further embodiments include an imaging system including a gantry having at least one imaging component for obtaining images of an object positioned within a bore of the gantry, the gantry having an imaging axis extending through the bore, the imaging system further including means for tilting the gantry to change an orientation of the imaging axis, means for displacing the gantry in a generally vertical direction with respect to the object, and means for obtaining image data of the object using the at least one imaging component. The imaging system may further include means for displacing the gantry in a generally horizontal direction with respect to the object.

BRIEF DESCRIPTION OF THE DRAWINGS

Other features and advantages of the present invention will be apparent from the following detailed description of the invention, taken in conjunction with the accompanying drawings of which:

FIG. 5A-5C illustrate an embodiment imaging system performing an imaging scan along a tilted axis.

FIGS. 8A-8C illustrate an embodiment x-ray CT imaging system performing a scan of a patient in a vertical direction.

FIGS. 10A-10C illustrate an x-ray CT imaging system performing a scan of a patient along a tilted axis.

DETAILED DESCRIPTION

This application is related to U.S. application Ser. No. 12/576,681, filed Oct. 9, 2009, now U.S. Pat. No. 8,118,488, U.S. application Ser. No. 13/025,566, filed Feb. 11, 2011, U.S. application Ser. No. 13/025,573, filed Feb. 11, 2011, U.S. application Ser. No. 13/441,555, filed Apr. 6, 2012, and U.S. Provisional Application No. 61/658,650, filed Jun. 12, 2012. The entire contents of all of these applications are hereby incorporated by reference for all purposes.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1A:
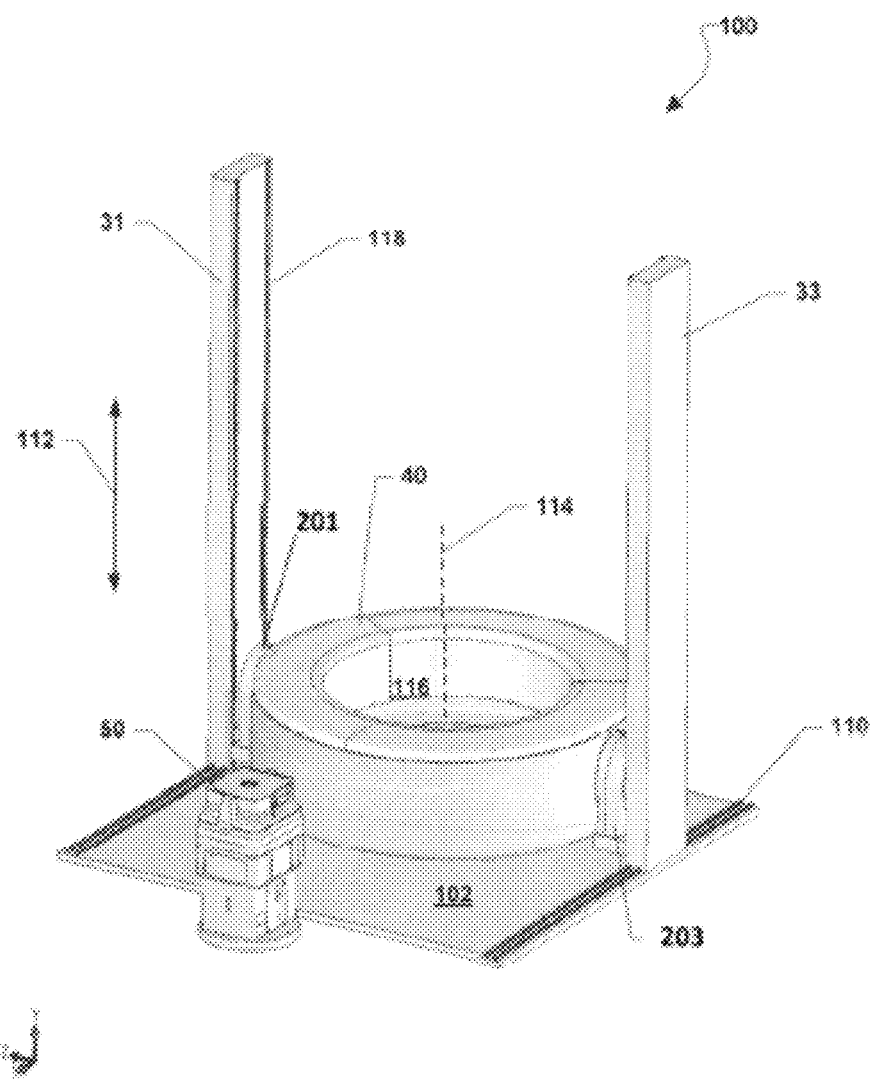
FIG. 1A is a perspective view of an X-ray CT imaging system with a vertically displaceable gantry ring in accordance with one embodiment of the invention.

Referring to FIG. 1A, an imaging system 100 according to one embodiment of the invention is shown. The system 100 includes image collection components, such as a rotatable x-ray source and detector array or stationary magnetic resonance imaging components, that are housed within the gantry 40. The system 100 is configured to collect imaging data, such as, for example x-ray computed tomography (CT) or magnetic resonance imaging (MRI) data, from an object located within the bore 116 of the gantry 40, in any manner known in the medical imaging field.

The system 100 may include a base 102, which may be a stable, high-strength support structure having a generally flat top surface. The base 102 may be supported on a suitable weight-bearing surface, such as on the ground or on a floor of a building. At least one support column 31, 33 may extend in a generally vertical direction from the base 102, and the gantry 40 may be attached to and supported above the base 102 by the at least one support column 31, 33. In the embodiment shown in FIG. 1A, two support columns 31, 33 (e.g., support posts or rails) are supported by the base 102 and extend in a generally vertical direction from the top surface of the base 102. The support columns 31, 33 are each attached to opposite sides of the gantry 40. The support columns 31, 33 may be attached to opposite sides of the gantry by attachment mechanisms 201, 203, as described in further detail below. It will be understood that more than two support columns (e.g., 3 or more), or a single support column may support the gantry above the base 102 in various embodiments. Also, in various embodiments, the base 102 may be omitted, and the at least one support column 31, 33 may be directly supported on the ground or floor.

In further embodiments, the at least one support column 31, 33 may be supported by a ceiling, a wall or other support structure, and may be hung or cantilevered from the support structure in a generally vertical orientation.

In various embodiments, the system 100 may be a fixed room (e.g., not mobile) imaging system. Alternatively, the system may be a mobile system that includes suitable means for transporting the entire system 100 (e.g., a drive mechanism coupled to one or more wheels, casters, rollers, etc.). The system 100 may further include a table column 50 for supporting one or more support tables, as described in further detail below.

As shown in FIG. 1A, the gantry 40 comprises a generally O-shaped structure having a central imaging bore 116. The bore 116 defines a central imaging axis 114. In various embodiments, the at least one support column 31, 33 may support the gantry 40 such that the imaging axis 114 has a generally vertical orientation. By generally vertical orientation, the imaging axis 114 may be normal to the flat top surface of base 102 or other planar horizontal surface on which the system 100 is supported (e.g., the ground or floor), and includes deviations up to 45° from the normal orientation (e.g., the imaging axis 114 is oriented at no more than 45° relative to the horizontal top surface of base 102).

The gantry 40 may be displaceable relative to at least one support column 31, 33. In embodiments, the gantry 40 may be displaceable along at least one dimension of the at least one support column 31, 33, such as along a length of the at least one support column 31, 33. In embodiments, the at least one support column 31, 33 may have a generally vertical orientation, and the gantry 40 may be displaceable in a generally vertical direction, such as the direction indicated by arrow 112 in FIG. 1A. By generally vertical orientation, the direction of displacement 112 may be normal to the flat top surface of base 102 or other planar horizontal surface on which the system 100 is supported (e.g., the ground or floor), and includes deviations up to 45° from the normal orientation (e.g., the direction of gantry displacement 112 is oriented at an angle more than 45° relative to the horizontal top surface of base 102).

The gantry 40 and the at least one support column 31, 33 may include mating features that enable the displacement of the gantry 40 relative to the support column(s) 31, 33 in a generally vertical direction 112, while the gantry 40 is restricted from moving in other directions relative to the support column(s) 31, 33. In the embodiment of FIG. 1A, the support column 31, 33 may each include rail(s) 118 extending along the length of the support column 31, 33. The gantry 40, or in the embodiment shown in FIG. 1A, the attachment mechanisms 201, 203, may include features that mate with the respective rails 118 to enable the displacement of the gantry 40. A first drive mechanism may drive the displacement (movement) of the gantry 40 relative to the support member(s) 31, 33. The first drive mechanism may comprise, for example, a traction drive, a gear system, a belt drive, a pulley, a drivewheel, etc., or various combinations thereof. The first drive mechanism may be mechanically coupled to and driven by one or more motor(s), which may be located on the gantry 40 and/or on one or more support columns 31, 33. A controller may control the operation of the motorized drive mechanism and thereby control the displacement of the gantry 40. The controller may receive position feedback signals indicative of the relative position of the gantry 40 and the one or more support columns 31, 33, such as from a linear encoder.

Figure 1B:
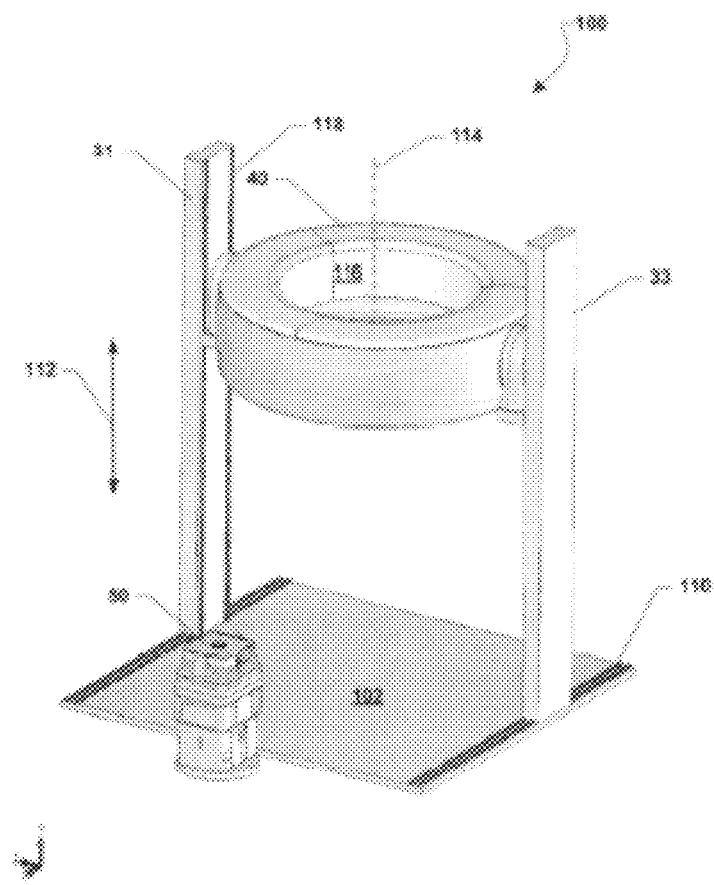
FIG. 1B illustrates the imaging system of FIG. 1A with the gantry ring in a raised position.

In embodiments, the gantry 40 may be vertically displaced along substantially the entire length of the support columns 31, 33. FIG. 1B illustrates the system of FIG. 1A with the gantry 40 displaced along the direction of arrow 112 to a height above the base 102 and floor. In embodiments, the gantry 40 may be displaceable from a first position proximate to the base 102 and floor of a room to a second position proximate the ceiling of the room. In some embodiments, the gantry 40 may be further displaceable into the ceiling, such as into a cavity or enclosure formed in the ceiling. Alternatively, or in addition, the gantry 40 may be displaceable into the base 102 and/or floor, such as in a cavity or enclosure formed in the base 102 and/or the floor. The respective cavities or enclosures may include doors or panels that can be closed to fully house the gantry within the cavity or enclosure. In this way, the gantry 40 may be moved completely out of the way and safely stored when not in use. The support columns 31, 33 may also be retracted into the floor and/or ceiling, such as in a telescoping fashion, or otherwise removed, when the system is not in use.

The imaging components of the gantry 40 may obtain imaging data of an object positioned within the bore 116 while the gantry 40 is displaced in a generally vertical direction to obtain a vertical scan of the object. For an x-ray CT imaging system, for example, an x-ray source and detector may rotate within the gantry 40 while the gantry is vertically displaced to provide a helical scan in a generally vertical orientation. In various embodiments, the system 100 may perform a helical scan of a human or animal patient in a weight bearing standing position.

Various examples of diagnostic imaging applications that may be performed on a human or animal patient in a weight-bearing position using the present system include, without limitation:

Imaging the bones of a foot. The three-dimensional relationships of the bones in the foot in a flatfoot deformity are difficult to assess with standard radiographs. CT scans demonstrate these relationships but are typically made in a non-weightbearing mode. The use of a weightbearing CT or other imaging apparatus may be useful in imaging the feet in patients with severe flexible pesplanus deformities and to better define the anatomical changes that occur.

Imaging of a limb (e.g. leg). Weight-bearing (CT) bilateral long leg hip to ankle examination and non-weight bearing cross-sectional imaging (CT) of the affected limb may be performed on the hip, knee and ankle, for example, and may be useful for determining variations in angulation and alignment accuracy for diagnosis and/or surgical planning Imaging of a spine. Weight bearing scanning (e.g., CT scanning) may be useful for improvements in the accurate diagnosis of degenerative spinal disorders by scanning a patient in the "real life" standing position. By scanning in the standing position, the spinal disc and facet joint compresses, which may enable more specific and precise diagnosis of degenerative spine disorders.

Imaging of a joint (e.g., knee). Weight bearing scanning (e.g., CT scanning) of the knee may enable more specific and precise diagnosis of the patella-femoral kinematics and may also be useful in surgical planning.

Angiography. Weight bearing angiography (e.g., CT angiography) may enable more accurate diagnosis, and may be used, for example, to examine the pulmonary arteries in the lungs to rule out pulmonary embolism, a serious but treatable condition. Weight bearing angiography may also be used to visualize blood flow in the renal arteries (those supplying the kidneys) in patients with high blood pressure and those suspected of having kidney disorders. Narrowing (stenosis) of a renal artery is a cause of high blood pressure (hypertension) in some patients and can be corrected. A special computerized method of viewing the images makes renal CT angiography a very accurate examination. This is also done in prospective kidney donors. Weight bearing angiography may also be used to identify aneurysms in the aorta or in other major blood vessels. Aneurysms are diseased areas of a weakened blood vessel wall that bulges out—like a bulge in a tire. Aneurysms are life-threatening because they can rupture. Weight bearing angiography may also be used to identify dissection in the aorta or its major branches. Dissection means that the layers of the artery wall peel away from each other—like the layers of an onion. Dissection can cause pain and can be life-threatening. Weight bearing angiography may also be used to identify a small aneurysm or arteriovenous malformation inside the brain that can be life-threatening. Weight bearing angiography may also be used to detect atherosclerotic disease that has narrowed the arteries to the legs.

Figure 2:
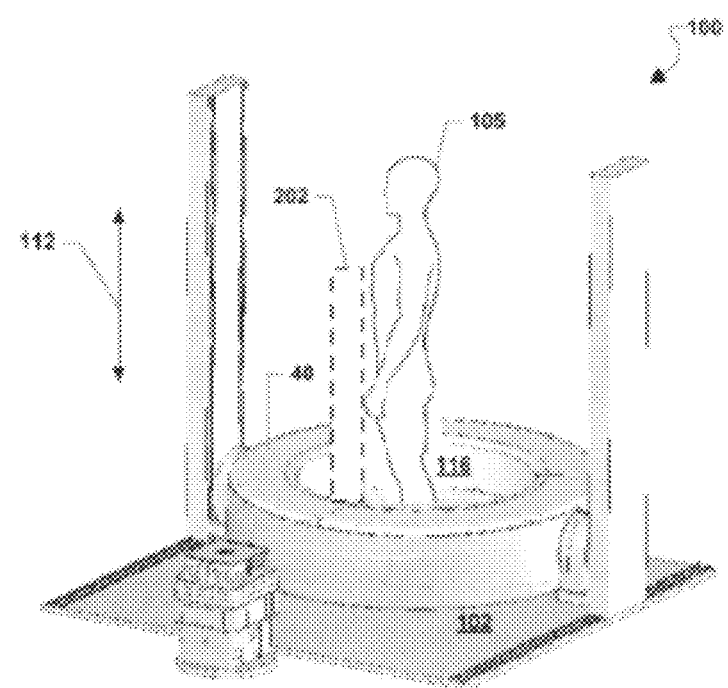
FIG. 2 illustrates an embodiment imaging system imaging a patient in a weight-bearing standing position.

FIG. 2, for example, illustrates a patient 105 in a standing position within an embodiment imaging system 100. The patient 105 is standing on the base 102 within the bore 116 of the gantry 40. The system 100 may be used to perform an imaging scan of the patient 105 in a generally vertical direction, as indicated by arrow 112. In embodiments, the system 100 may scan any portion of the patient's anatomy, including a full-body scan. The system 100 may also be used to perform a vertical scan of a patient in a sitting position or a reclined position.

In embodiments, the system 100 may include at least one patient/object support structure 202 that may extend from the base 102 in a generally vertical direction. The support structure 202 may be aligned with the bore 116. The support structure 202 may be made of a radiolucent (x-ray transparent) material. As shown in FIG. 2, a support structure 202 may be radiolucent (x-ray transparent) vertical rigid post or plate that the patient 105 may grab or sit on to help stabilize the patient throughout the scan. The support structure 202 may have handles or arm rests at varying heights to help the patient lean against and stay motionless during the scan. The support structure 202 may also be a post with a radiolucent chair for people who have a hard time standing during a scan, or it may be two plates that sandwich the patient in a vertical standing position to help the patient remain still during a scan.

The support structure 202 may be made entirely or partially of any radiolucent material such as carbon fiber, etc.

Figure 3A:
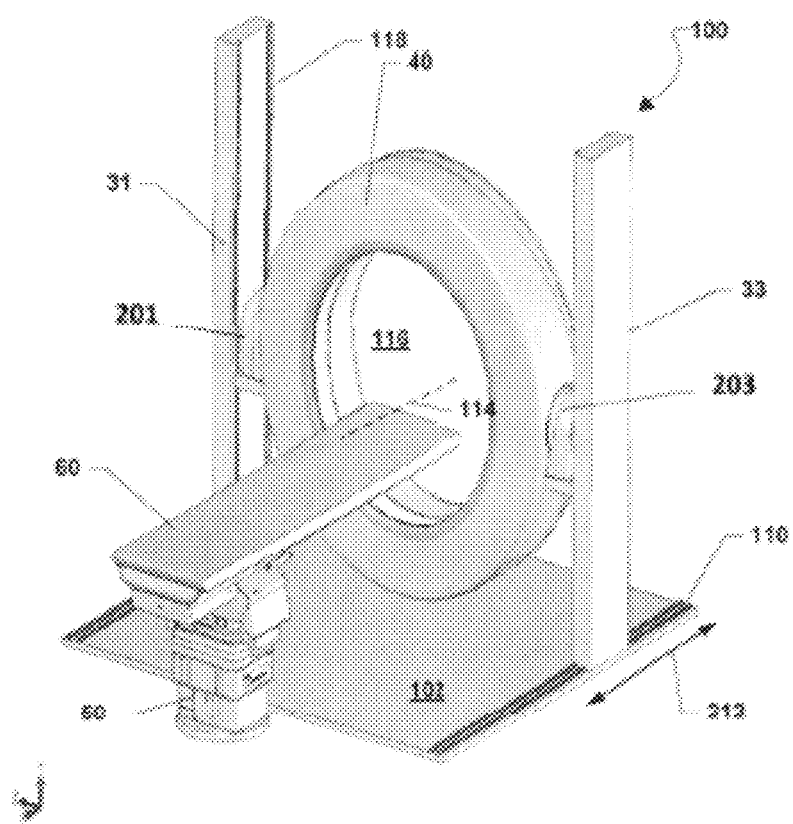
FIG. 3A illustrates an embodiment imaging system in which the gantry has been pivoted from a vertical orientation to a horizontal orientation, with the gantry horizontally displaced from a table column and support table.
Figure 3B:
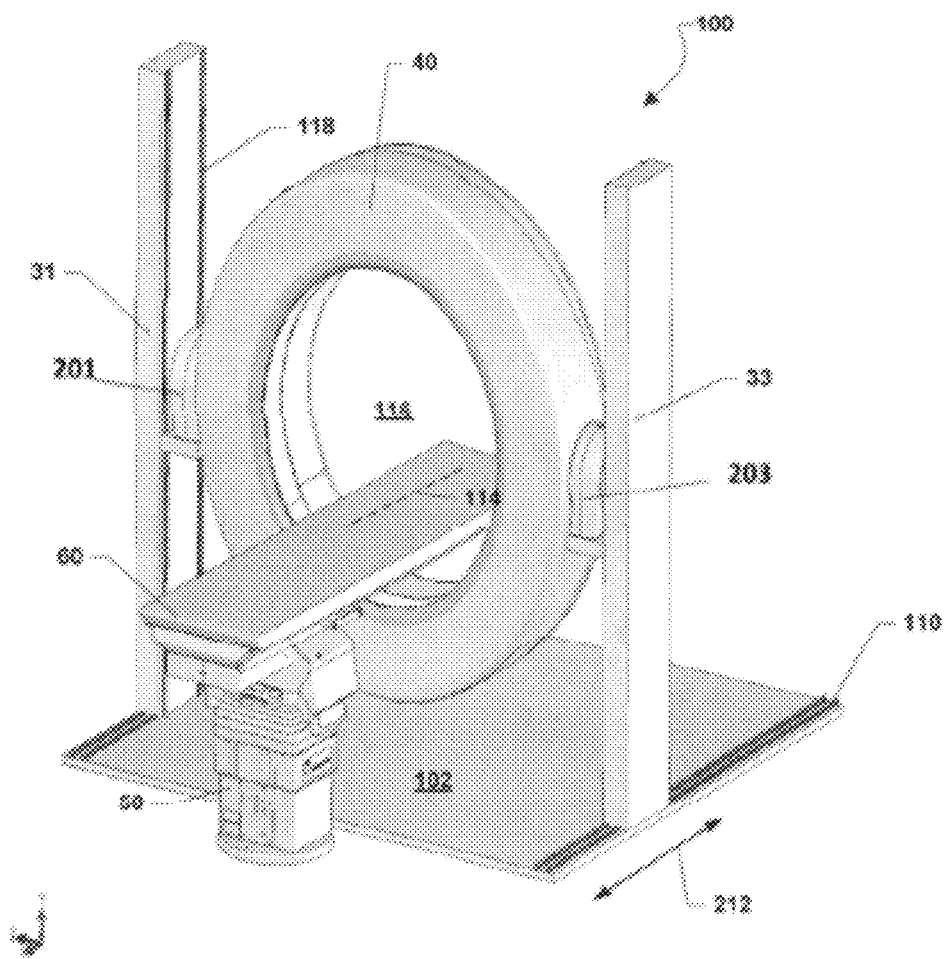
FIG. 3B illustrates the imaging system of FIG. 3A with the gantry translated in a horizontal direction (along z-axis) towards the table column and support table.
Figure 3C:
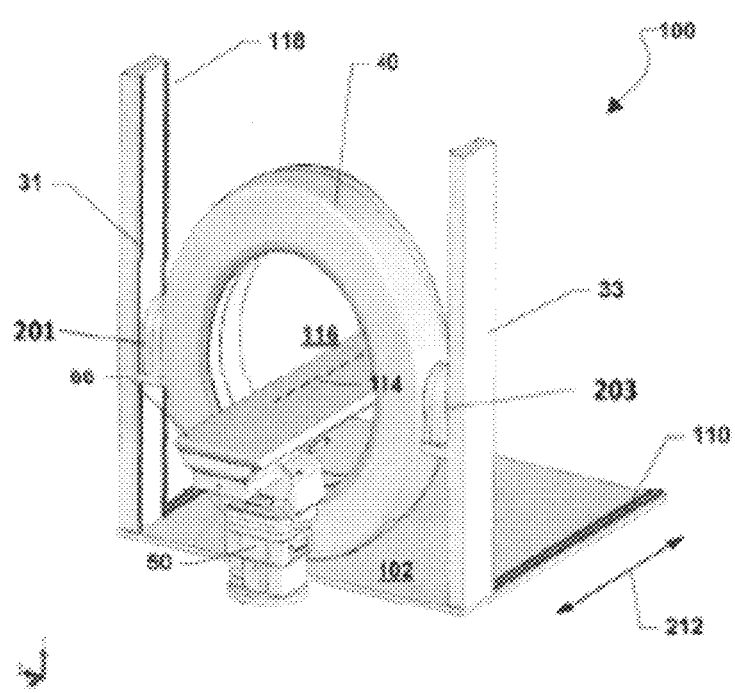
FIG. 3C illustrates the imaging system of FIG. 3A further translated in a horizontal direction (along z-axis) towards the table column and support table.

In embodiments, the gantry 40 may be attached to the at least one support column 31, 33 such that the gantry 40 may pivot or tilt with respect to the support column(s) 31, 33. As shown in FIG. 1A, for example, the gantry 40 may be attached to the support columns 31, 33 by respective attachment mechanisms 201, 203. The attachment mechanisms 201, 203 may include a bearing assembly that allows the gantry 40 to pivot with respect to the support columns 31, 33. In an alternative embodiment, the gantry 40 may be directly attached to the support columns 31, 33 (e.g., without a separate attachment mechanism 201, 203 as shown in FIG. 1A) via a bearing assembly (not illustrated) that enables the gantry 40 to pivot with respect to the support columns. In embodiments, the gantry 40 may pivot at least about 45° relative to the support columns 31, 33. In preferred embodiments, the gantry 40 may pivot more than 45°, such as at least about 90°, relative to the support columns 31, 33. In some embodiments, the gantry 40 may pivot between a generally vertical orientation (such as shown in FIGS. 1A-B) and a generally horizontal orientation, as shown in FIGS. 3A-C. By generally horizontal orientation, the imaging axis 114 may be parallel to the flat top surface of base 102 or other planar horizontal surface on which the system 100 is supported (e.g., the ground or floor), and includes deviations up to 45° from this parallel orientation (e.g., the imaging axis 114 is oriented less than 45° relative to the horizontal top surface of base 102).

In a generally horizontal configuration, the system 100 may perform an imaging scan of an object positioned on a suitable support, such as tabletop support 60, shown in FIGS. 3A-C. The table column 50 may be configured to support the tabletop support 60. The tabletop support 60 may be attached to the table column 50 in a cantilevered manner, such that at least a portion of the tabletop support 60 may extend over the base. A portion of the tabletop support 60 may extend into the bore 116 of the gantry 60. The tabletop support 60 may include, for example, any suitable table, such as a patient table, as well as a chair for a seated patient.

An imaging scan may be performed via a relative displacement of the gantry 40 and the tabletop support 60. The relative displacement may be in a generally horizontal direction, such as indicated by arrow 212. The relative displacement may be the displacement of the tabletop support 60, such as a displacement of the table column 50 and tabletop support 60 with respect to a stationary gantry 40, or a displacement of the tabletop support 60 with respect to a stationary table column 50 and gantry 40. In other embodiments, the gantry 40 may move relative to a stationary tabletop support 60. In further embodiments, both the gantry 40 and the tabletop support 60 may move.

In the embodiment illustrated in FIGS. 3A-3C, the gantry 40 and the at least one support column 31, 33 may be displaced relative to the base 102, table column 50 and patient table 60, which may be stationary. The base 102 and the at least one support column 31, 33 may include mating features that enable the displacement of the support members 31, 33 (along with the gantry 40 and attachment mechanisms 201, 203 to which they are attached), relative to base 102 in a generally horizontal direction 212, while the support column(s) 31, 33 and gantry 40 are restricted from moving in other directions relative to base 102. In the embodiment of FIGS. 3A-C, the base 102 may include a horizontal guide in the form of rails 110 extending along the length of the base 102. The support columns 31, 33 may include features that mate with the respective rails 110 to enable the horizontal displacement of the support columns 31, 33 and gantry 40. A second drive mechanism (e.g., z-drive) may drive the displacement (movement) of the support columns 31, 33, attachment mechanisms 201, 203 and gantry 40 along the base 102. The second drive mechanism may comprise, for example, a traction drive, a gear system, a belt drive, a pulley, a drivewheel, etc., or various combinations thereof. The second drive mechanism may be mechanically coupled to and driven by one or more motor(s), which may be located on the base 102 and/or on one or more support column(s) 31, 33. A controller may control the operation of the motorized second drive mechanism and thereby control the displacement of the support columns 31, 33 and gantry 40. The controller may receive position feedback signals indicative of the position of the support column(s) 31, 33 and gantry 40 relative to the base 102, such as from a linear encoder.

The drive mechanism for vertical displacement as described above may be used to adjust the height of the gantry 40 relative to the tabletop support 60, either before or during a horizontal scan. Similarly, the drive mechanism for horizontal displacement as described above may be used to adjust the position of the gantry 40 in a horizontal direction (e.g., z-direction), either before or during a vertical scan.

FIGS. 3A-C illustrate an embodiment of a system 100 performing a horizontal scan. In FIG. 3A, the gantry 40 and support columns 31, 33 are located away from the table column 50 and the distal end of the tabletop support 60 is within the bore 116. In FIG. 3B, the gantry 40 and support columns 31, 33 are moved towards the table column 50 in the direction of arrow 212, and the tabletop support 60 extends fully through the bore 116. In FIG. 3C, the gantry 40 and support columns 31, 33 have traveled to the proximal end of rails 110, and the gantry 40 is proximate to the table column 50. The imaging components of the gantry 40 may obtain imaging data of an object positioned within the bore 116 while the gantry 40 is displaced in a generally horizontal direction, as shown in FIGS. 3A-C, to obtain a horizontal scan of the object. For an x-ray CT imaging system, for example, an x-ray source and detector may rotate within the gantry 40 while the gantry is horizontally displaced to provide a helical scan in a generally horizontal orientation. In various embodiments, the system 100 may perform a horizontal scan of a human or animal patient in a lying position.

Figure 4:
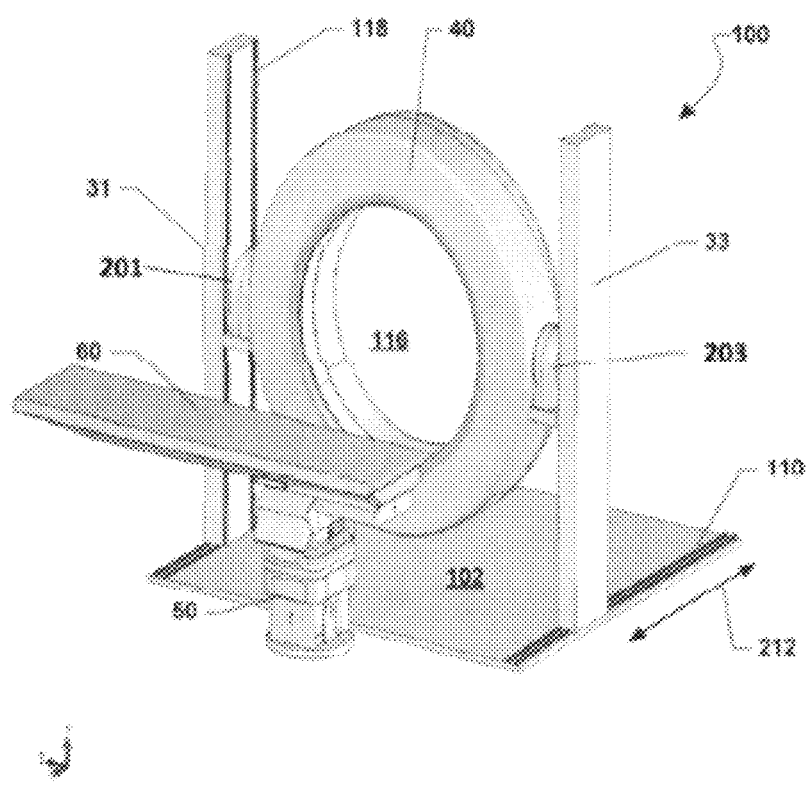
FIG. 4 illustrates the support table rotated 90 degrees on the table column.
Figure 6A:
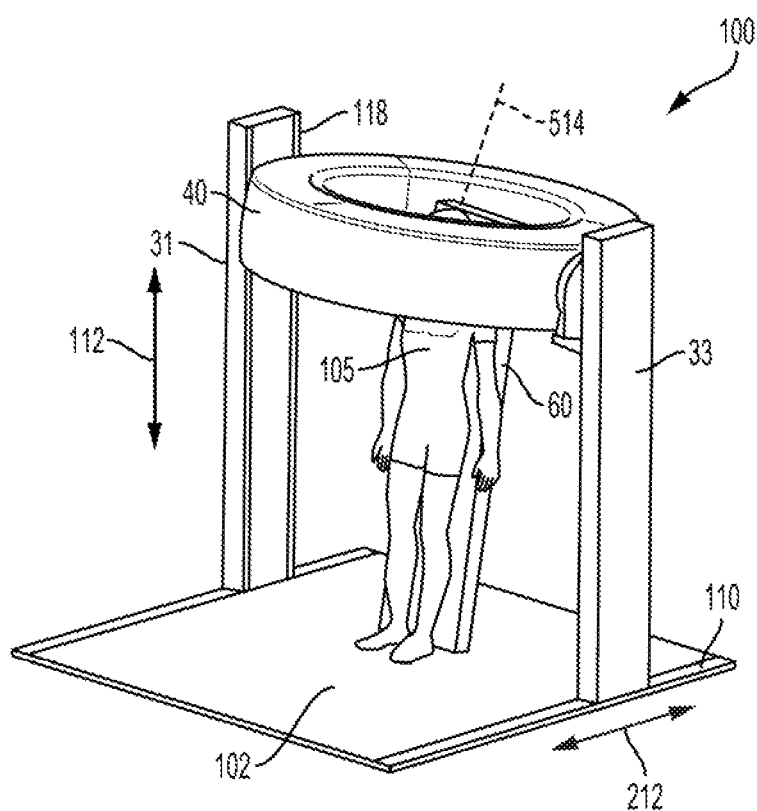
FIG. 6 illustrates a plurality of components housed within the gantry according to one embodiment.

FIG. 4 illustrates a system 100 according to one embodiment wherein the tabletop support 60 may be rotated at least about 90° on the table column 50. In embodiments, the tabletop support 60 may be rotated to facilitate loading/unloading of a patient, or to provide better access to the patient for a medical procedure. The tabletop support 60 may be rotated back to the orientation of FIGS. 3A-C in order to perform an additional imaging scan, without having to remove the patient or move the patient relative to the tabletop support 60 between scans. The tabletop support 60 may be rotated to the orientation of FIG. 4 to perform a scan in a generally vertical orientation, such as shown in FIGS. 1A-2. In embodiments, the tabletop support 60 may also translate with respect to the table column 50 in one or more directions. The height of the table column 50 may also be adjustable.

Figure 5B:
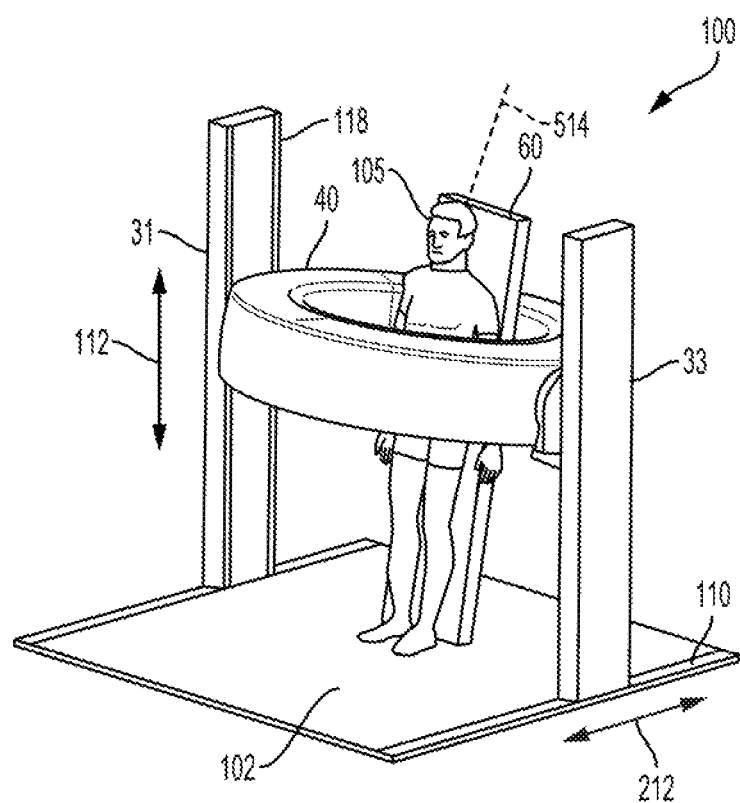
Figure 5C:
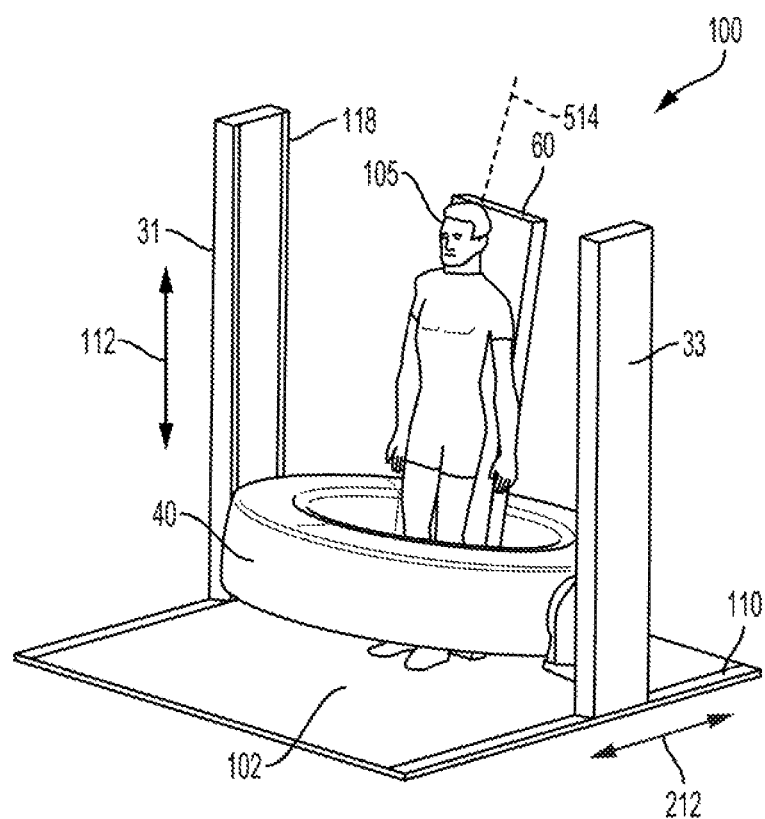

FIGS. 5A-5C illustrate an embodiment imaging system 100 performing a scan along a tilted axis. In FIG. 5A, the object being imaged (e.g., patient 105) is positioned along a tilted axis 514 (i.e., neither horizontal nor vertical). The patient 105 may be supported against a support structure 60 that is similarly aligned along tilted axis 514. The gantry 40 may be tilted on the support columns 31, 33 to any desired angle relative to axis 514, and may be perpendicular to axis 514. The region of interest of the patient 105 may be centered within the bore (e.g., such that the bore imaging axis is collinear with the tilted axis 514). In various embodiments, the imaging system 100 may perform an imaging scan (e.g., a helical x-ray CT scan) of the patient 105 while maintaining a fixed angle between the gantry and the tilted axis 514 and maintaining the region of interest centered within the bore. The imaging system 100 may achieve this via coordinated movement of the gantry in both a vertical direction (indicated by arrow 112) and a horizontal direction (indicated by arrow 212). The vertical movement of the gantry 40 may be with respect to the support column(s) 31, 33, and may be along vertical rail(s) 118, as described above. The horizontal movement of the gantry 40 may be the movement of the support column(s) 31, 33, attachment mechanisms 201, 203 and gantry 40 along the base 102, and may be along a horizontal guide (rail(s) 110), as described above. A control system of the imaging system 100 may include logic configured to determine the relative vertical and horizontal displacement of the gantry 40 needed to translate the gantry along a tilted axis 514. First and second drive mechanism(s) for producing the respective vertical and horizontal movements of the gantry 40 may be controlled by the control system to provide coordinated vertical and horizontal displacement of the gantry. Where the angle of the tilted axis 514 is known or may be determined, the control system may use simple trigonometric relations to determine the vertical and horizontal displacement of gantry 40. For example, where the tilted axis 514 is at a 60° angle relative to horizontal, each cm of the scan along axis 514 may include a vertical displacement of ~0.87 cm (i.e., sin 60°) and a horizontal displacement of 0.5 cm (i.e., cos 60°). Thus, the imaging system 100 may perform a scan at any tilt axis 514, and in embodiments may perform scans along complex axes, such as along an angled or curved axis.

FIGS. 5A-5C illustrate an example of an imaging scan of a patient along a tilted axis 514. The patient 105 may lean against support 60 such that the patient is aligned along the tilted axis 514. The gantry 40 may be tilted such that the gantry is perpendicular to tilted axis 514, with the patient centered within the bore of the gantry. The gantry 40 may then be displaced in both vertical and horizontal directions such that the gantry 40 may translate along the length of the patient 105, as shown in FIGS. 5B and 5C. The gantry 40 may remain perpendicular to the tilted axis 514 through the duration of the scan. Imaging components, such as an x-ray source and detector, may rotate within the gantry 40 while the gantry translates along the length of the patient 105 to obtain a helical scan.

Figure 6:
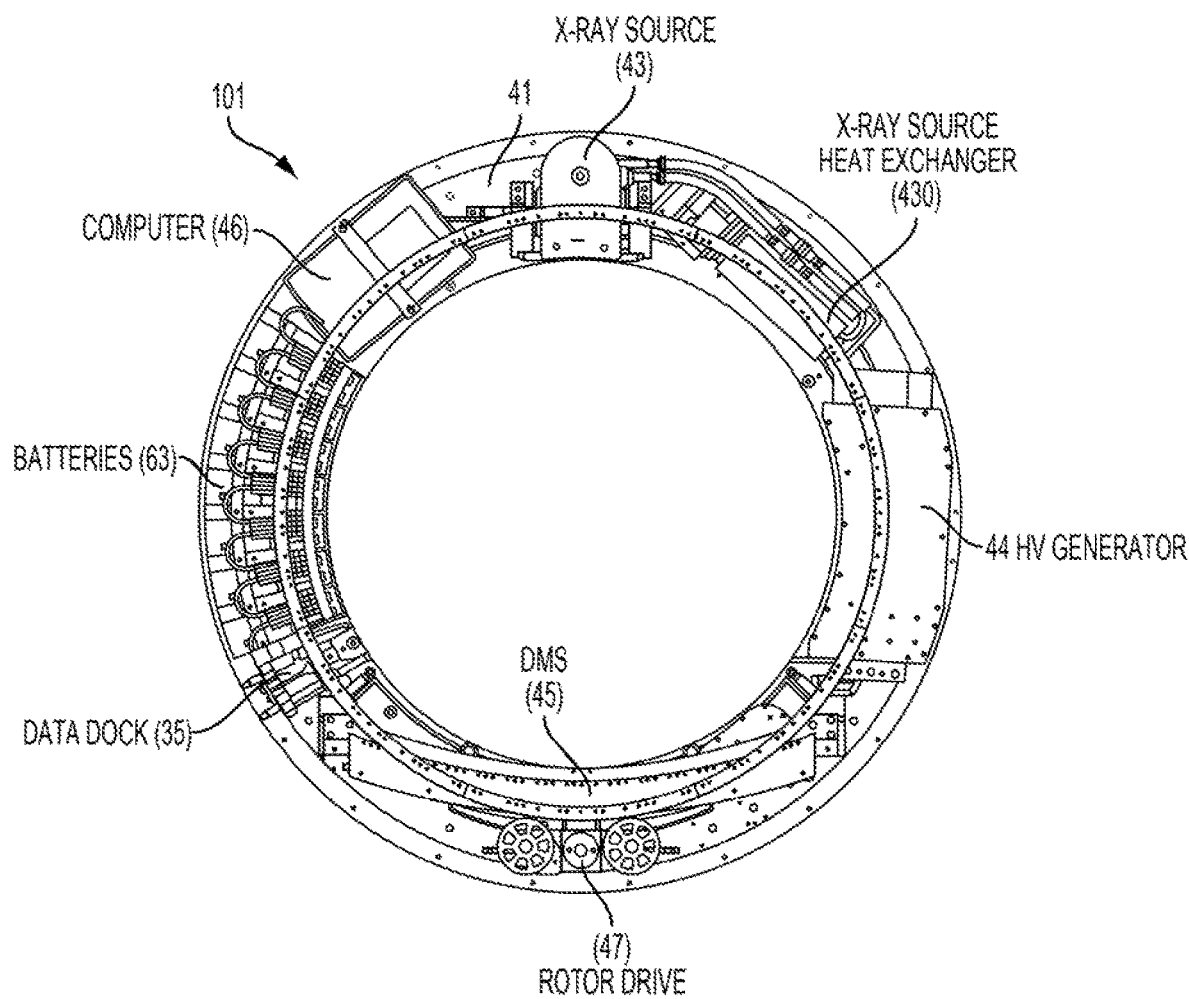

A number of imaging components that may be included in the imaging system 100 for providing an imaging scan are illustrated in FIG. 6. The components may be housed within the gantry 40. In one embodiment, the imaging system 100 comprises an X-ray CT imaging system, and includes an x-ray source 43, high-voltage generator 44, heat exchanger 430, x-ray detector 45, power supply 63 (e.g., battery system), computer 46, rotor drive mechanism 47, and a docking system 35 (e.g., for providing intermittent power/data connection between rotating and non-rotation portions of the system). These components may be mounted on a rotor 41 to collectively define a rotating portion 101 of the system. The rotor 41 and the components mounted thereto may rotate around a housing defined by an outer shell 42 (FIG. 7A) of the gantry 40 and within an internal cavity of the gantry 40.

It will be understood that the components described and illustrated are merely exemplary, and other embodiments may omit one or more of these components and may utilize other additional components. For example, in embodiments, power for the rotating portion 101 may be provided by a slip ring or cable system, so that a power supply 63 on the rotating portion 101 may not be needed. In some embodiments, power and/or data may be continuously transferred between the rotating and non-rotating portions via cable, slip ring or wirelessly, in which case the power supply 63, computer 46 and/or docking system 35 may not be included. Further, the rotation of the rotor may be provided by a drive system on the non-rotating portion, in which case the rotor drive mechanism 47 on the rotor 41 may not be included. Also, it will be understood that other types of imaging systems, such as MRI systems, may use other suitable components for imaging, as are known in the art.

In embodiments, the x-ray source 43 and detector 45 may be configured to perform a helical x-ray CT scan. The detector 45 may comprise a plurality of x-ray sensitive detector elements arranged in a semicircular arc, with the arc center coinciding with the focal spot of the x-ray source. In some embodiments, the x-ray detector may be a flat panel detector, and the system may be configured to perform real time x-ray and/or cone beam imaging of an object within the bore of the gantry. The system may be a single plane system (i.e., having a single source and detector which can obtain an image in a single plane at one time), or in some embodiments, may be a bi-plane or multi-plane system (i.e., having multiple x-ray source(s) and/or detector(s) at different positions on the ring for obtaining images in multiple planes at the same time).

In the embodiment of FIG. 6, during an imaging scan, the rotor 41 rotates within the interior of the gantry, while the imaging components such as the x-ray source 43 and x-ray detector 45 obtain imaging data for an object positioned within the bore 116 of the gantry, as is known, for example, in conventional X-ray CT scanners. The rotor drive mechanism 47 may drive the rotation of the rotor 41 around the interior of the gantry 40. The rotor drive mechanism 47 may be controlled by a system controller that controls the rotation and precise angular position of the rotor 41 with respect to the gantry 40, preferably using position feedback data, such as from a position encoder device.

Various embodiments of the imaging system 100 may be relatively compact. One way in which the system 100 may be made compact is in the design of the gantry 40 and its interface with the rotating portion 101 (e.g., the rotor 41 and the various components mounted to the rotor 41). In embodiments, the outer shell 42 of the gantry 40 may comprise both a protective outer covering for the rotating portion 101 and a mounting surface for a bearing that enables the rotating portion 101 to rotate 360° within the outer shell 42 of the gantry 40.

Figure 7A:
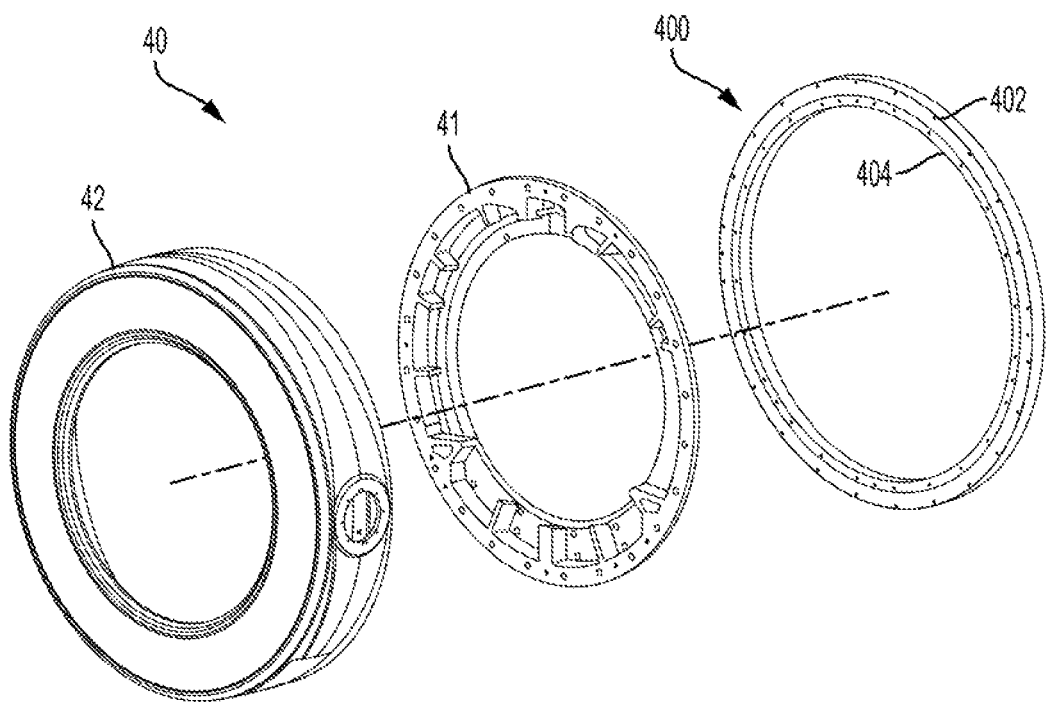
FIG. 7A is an exploded view of a gantry illustrating an outer shell, a rotor and a bearing system according to one embodiment.
Figure 7B:
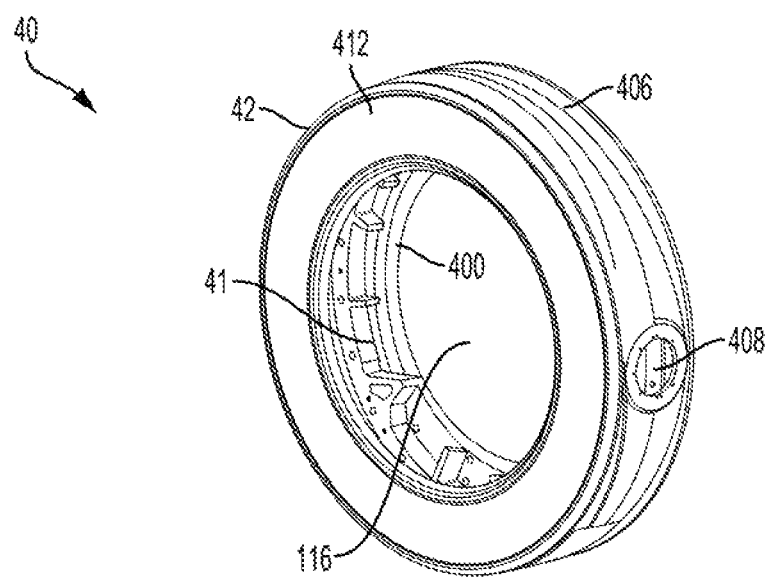
FIG. 7B is a perspective view of the assembled gantry.

FIG. 7A is an exploded view of a gantry 40 according to one embodiment that illustrates the outer shell 42, the rotor 41 and a bearing assembly 400. FIG. 7B illustrates the assembled gantry 40. As is shown in FIGS. 7A-B, the outer shell 42 of the gantry 40 may be a generally O-shaped covering of a structural material that may at least substantially fully enclose the rotating portion 101, including the rotor 41 and any components mounted to the rotor, over one or more sides of the rotating portion 101. The outer shell 42 of the gantry 40 may be conceptually considered an "exoskeleton," that both supports the rotating portion 101 of the system 100, preferably in three dimensions, and also provides a protective barrier between the rotating portion 101 and the external environment. The outer shell 42 may be fabricated from a sufficiently rigid and strong structural material, which may include, for example, metal, composite material, high-strength plastic, carbon fiber and combinations of such materials. In preferred embodiments, the outer shell 42 may be comprised of a metal, such as aluminum. The outer shell 42 may be machined or otherwise fabricated to relatively tight tolerances. The outer shell 42 may be formed as a one piece, unitary component. In other embodiments, the outer shell 42 may be comprised of multiple components and/or materials that may be joined using any suitable technique to provide the shell 42.

The outer shell 42 may have an outer circumferential surface 406 that may extend around the periphery of the rotating portion 101 of the system 100 to substantially fully enclose the rotating portion 101 around its outer circumference. The outer shell 42 may also include at least one side wall 412 that may extend from the outer circumferential surface 406 to a bore 116 of the gantry 40 and may substantially fully enclose the rotating portion 101 around one side of the rotating portion.

The bearing assembly 400 according to one embodiment is shown in FIG. 7A. In this embodiment, the bearing assembly 400 includes a first race 402 that may be securely fastened to the outer shell 42 of the gantry 40, and a second race 404 that may be securely fastened to the rotor 41. A bearing element is provided between the first race 402 and the second race 404, and is configured to allow the second race 404 (along with the rotor 41 to which it is attached) to rotate concentrically within the first race 402, preferably with minimal friction, thereby enabling the rotor 41 to rotate with respect to the outer shell 42 of the gantry 40. In some embodiments, all or a portion of the bearing assembly 400 may be integrally formed as a part of the outer shell 42, of the rotor 41, or of both. For example, the first race 402 may be formed as an integral surface of the outer shell 42 and/or the second race 404 may be formed as an integral surface of the rotor 41. In various embodiments, the entire bearing assembly for enabling the rotation of the rotating portion 101 with respect to the non-rotating portion 103 of the imaging system 100 may be located within the generally O-shaped gantry 40.

The outer diameter of the gantry 40 can be relatively small, which may facilitate the portability of the system 100. In a preferred embodiment, the outer diameter of the gantry 40 is less than about 70 inches, such as between about 60 and 68 inches, and in one embodiment is about 66 inches. The outer circumferential wall 406 of the outer shell 42 may be relatively thin to minimize the OD dimension of the gantry 40. In addition, the interior diameter of the gantry 40, or equivalently the bore 116 diameter, can be sufficiently large to allow for the widest variety of imaging applications, including enabling different patient support tables to fit inside the bore, and to maximize access to a subject located inside the bore. In one embodiment, the bore diameter of the gantry 40 is greater than about 38 inches, such as between about 38 and 44 inches, and in some embodiments can be between about 40 and 50 inches. In one exemplary embodiment, the bore has a diameter of about 42 inches. The gantry 40 generally has a narrow profile, which may facilitate portability of the system 100. In one embodiment, the width of the gantry 40 (W) is less than about 17 inches, and can be about 15 inches or less.

Figure 7C:
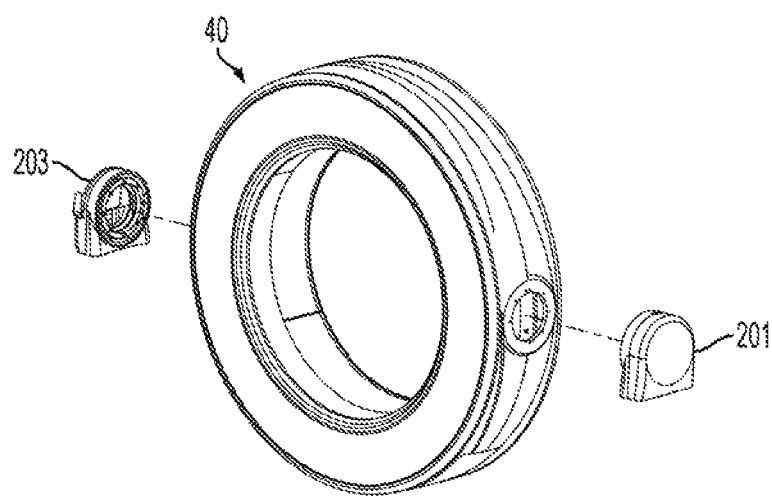
FIG. 7C schematically illustrates the assembly of the gantry according to one embodiment.

FIG. 7C illustrates the gantry 40 and attachment mechanisms 201, 203 for securing the gantry 40 to the support column(s) 31, 33 (see FIG. 1A). The attachment mechanisms 201, 203, which may have an "earmuff" shape, may include bearing apparatuses that enable the pivot motion of the gantry 40 relative to the support column(s) 31, 33, such as a pivot motion from a vertical to a horizontal orientation, and vice versa. One or both of the attachment mechanism(s) 201, 203 may also include a portion of a docking system for providing power and data transfer between rotating and non-rotating portions of the system. The system 100 may be assembled by securing the attachment mechanisms 201, 203 to opposite sides of the gantry 40. The entire assembly may then be attached to the support columns 31, 33.

FIGS. 8A-8C, 9A-9C and 10A-10C illustrate yet another embodiment of an imaging system 800. The imaging system 800 in this embodiment includes an imaging gantry 40 mounted to a support column 801. The support column 801 may be mounted to the gantry 40 on a first side of the gantry 40 and may support the gantry 40 in a cantilevered manner. The gantry 40 may be a generally O-shaped structure having a central imaging bore 116 and defining an imaging axis 114 extending through the bore. The gantry 40 may contain one of more of the components described above with reference to FIG. 6, such as an x-ray source, a detector, a high-voltage generator, a heat exchanger, a power supply (e.g., battery system), and a computer. These components may be mounted on a rotating element (e.g., a rotor) that rotates within the gantry 40 during an imaging scan. A rotor drive mechanism may also be located on the rotor, and may drive the rotation of the rotor. Between scans, a docking system may be used to couple the rotating and non-rotating portions of the system 800 for power and data communication.

The system 800 may also include a base 802 that may be located on a weight-bearing surface, such as a floor 819 of a building. In the illustrated embodiment, the base 802 comprises a generally rectilinear support structure that may be mounted (e.g., bolted) to the floor 819. The support column 801 may be located on and supported by the base 802 and may extend upwards from the top surface of the base 802 in a generally vertical direction. The support column 801 may have a length dimension that extends vertically at least about 2 meters, such as 2-5 meters (e.g., about 3 meters).

Figure 8B:
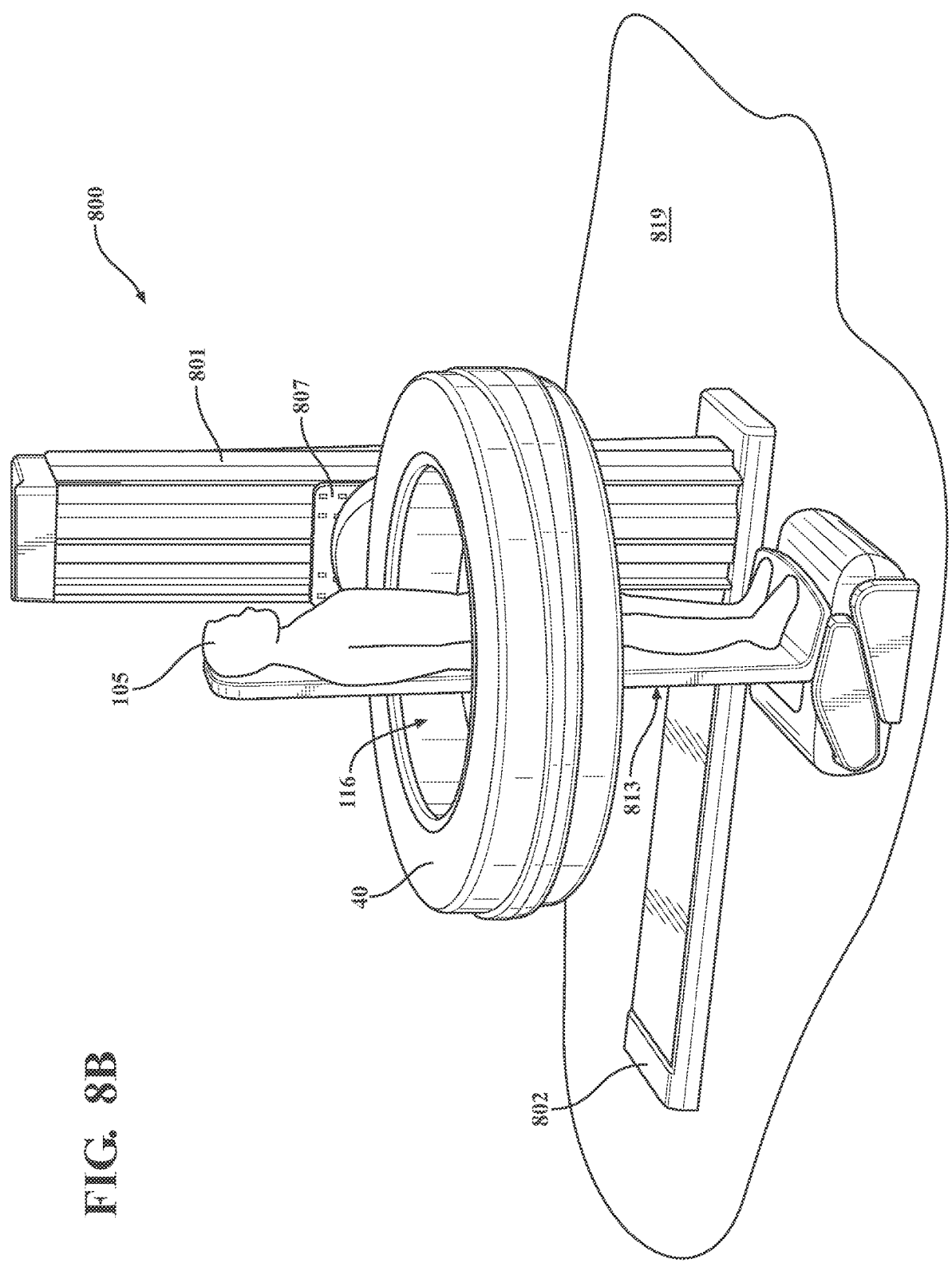

As shown in FIGS. 8A-8C, the support column 801 may support the gantry 40 in a generally vertical orientation, such that the front and rear faces of the gantry 40 extend parallel to the floor 819 and the imaging axis 114 through the gantry bore 116 extends in a vertical direction (i.e., perpendicular to the floor). The imaging axis 114 of the gantry 40 in this configuration may extend parallel to the length dimension of the vertically-extending support column 801.

The gantry 40 may be displaced along the length of the support column 801 in a generally vertical direction. This is illustrated in FIGS. 8A-8C, which show the gantry 40 displaced vertically from a first position in FIG. 8A with the gantry 40 located proximate a first end of the support column 801 (i.e., opposite the base 802), to a second position in FIG. 8B with the gantry 40 located approximately mid-way along the length of the support column 801, to a third position in FIG. 8C, with the gantry 40 located proximate to a second end of the support column 801 proximate to the base 802. The gantry 40 and the support column 801 may include mating features that confine the displacement of the gantry 40 along the length of the support column 801. As shown in FIGS. 8A-8C, for example, a pair of parallel vertical rails 805, 806 may extend in a vertical direction along the length of the support column 801. An attachment mechanism 807 may be attached to one side of the gantry 40, and may be located between the side of the gantry 40 and the support column 801. The attachment mechanism 807 may include bearing elements (e.g., roller and/or dovetail bearing slides) that engage with the vertical rails 805, 806 to provide linear motion of the attachment mechanism 807 and gantry 40 along the length of the support column 801.

Figure 10A:
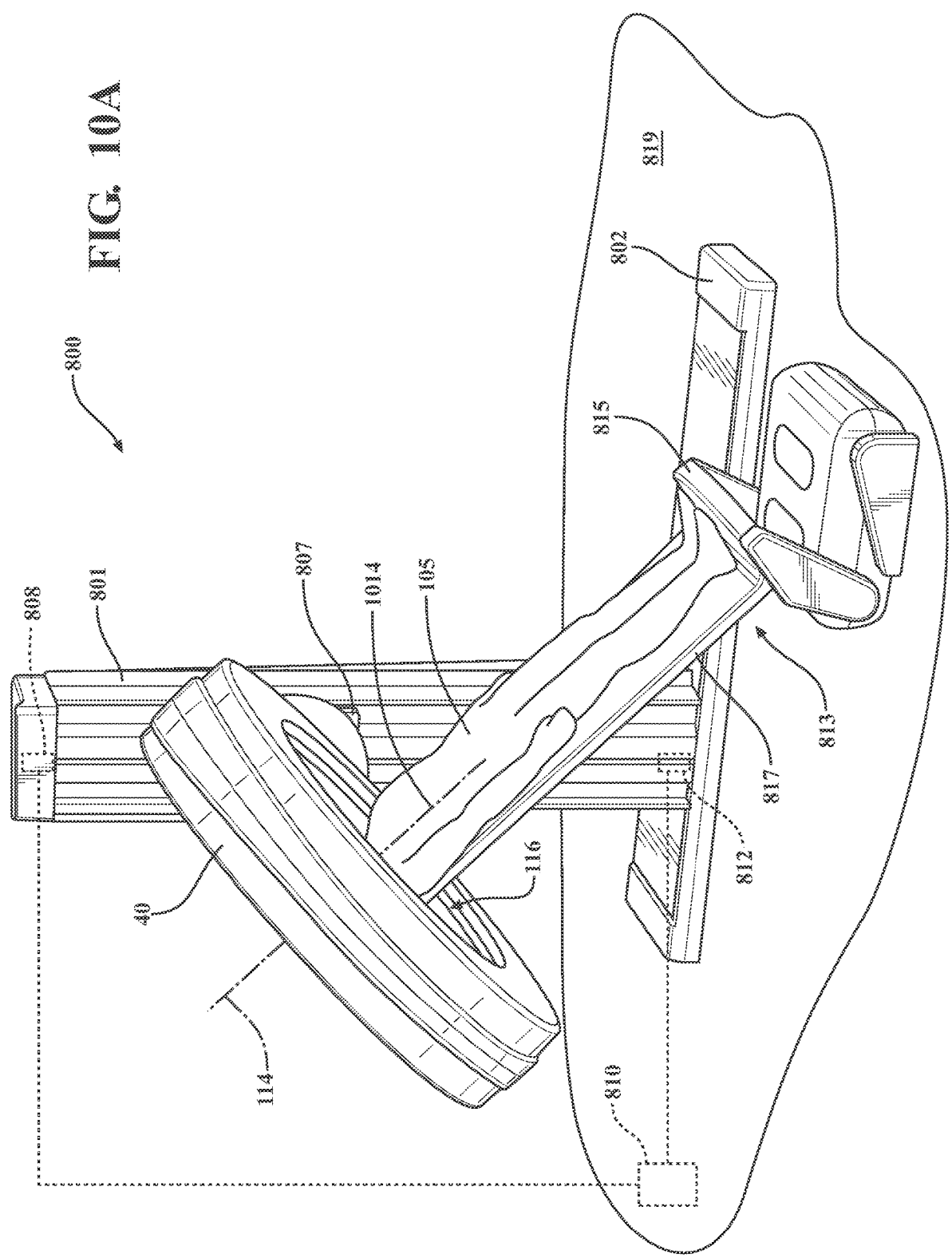

A first drive mechanism may drive the displacement of the gantry 40 and attachment mechanism 807 relative to the support column 801. A first drive mechanism 808 is schematically illustrated in FIG. 10A. The first drive mechanism 808 may comprise a linear actuator, such as a lead screw or ball screw system. In embodiments, a threaded shaft may extend lengthwise within an interior housing 809 of the support column 801. A motor, which may also be located within the support column 801, may be geared into the threaded shaft to drive the rotation of the shaft. An arm may extend from the attachment mechanism 807 through an opening 811 (e.g., a slot) extending along the length of the support column 801. A nut on the end of the arm may engage with the threaded shaft within the housing 809 of the support column 801. The rotation of the threaded shaft may cause the nut to reciprocate up and down along the length of the shaft. The reciprocation of the nut on the shaft may drive the vertical displacement of the attachment mechanism 807 and gantry 40 with respect to the support column 801. A controller 810 (see FIG. 10A) may control the operation of the first drive mechanism and thereby control the vertical displacement of the gantry 40. The controller may receive position feedback signals indicative of the position of the gantry 40 along the support column 801, such as from a linear encoder.

The system 800 may also include a patient support 813. The patient support 813 may support a patient 105 in a weight-bearing standing position as shown in FIGS. 8A-8C. The patient support 813 may include a first portion 815 that supports the feet of a patient upon which the patient 105 may stand. A second portion 817 may extend generally perpendicular to the first portion 815 and may provide additional support to the patient 105. For example, the patient 105 may lean against the second portion 817 during a scan and the second portion 817 may help to stabilize the patient 105 and prevent the patient 105 from falling off the patient support 813. In embodiments, the patient support 813 may support the patient 105 in a position that is raised above the floor 819, as shown in FIGS. 8A-8C. The first portion 815 and the second portion 817 may be made of a radiolucent (x-ray transparent) material, such as carbon fiber material.

The system 800 may be used to perform an imaging scan of a patient 105 in a weight-bearing standing position. For example, for an x-ray CT imaging system, the x-ray source and detector may rotate within the gantry 40 around the patient while the gantry 40 and attachment mechanism 807 are displaced vertically on the support column 801 as shown in FIGS. 8A-8C to perform a helical scan of a patient 105 positioned on the patient support 813. In embodiments, the system 800 may scan over the full length of the patient (e.g., from the top of the patient's cranium to the bottom of the patient's feet) or any selected portion thereof. Following a scan, the gantry 40 may be moved to an out-of-the way position (e.g., to the top of the support column 801 or below the patient's feet) and the patient 105 may be removed from the patient support 813.

Figure 9A:
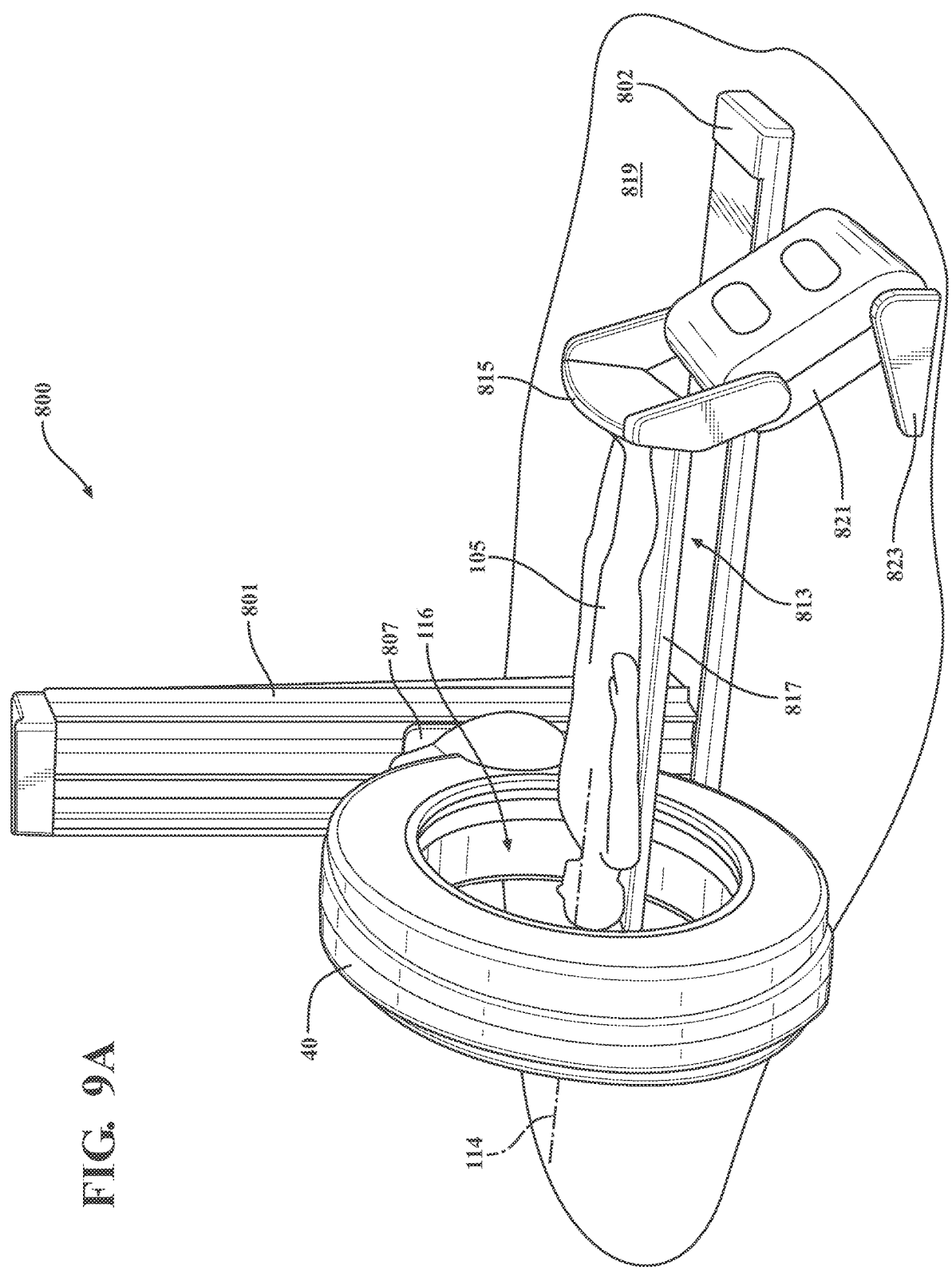
FIGS. 9A-9C illustrate an embodiment x-ray CT imaging system performing a scan of a patient in a horizontal direction.
Figure 9B:
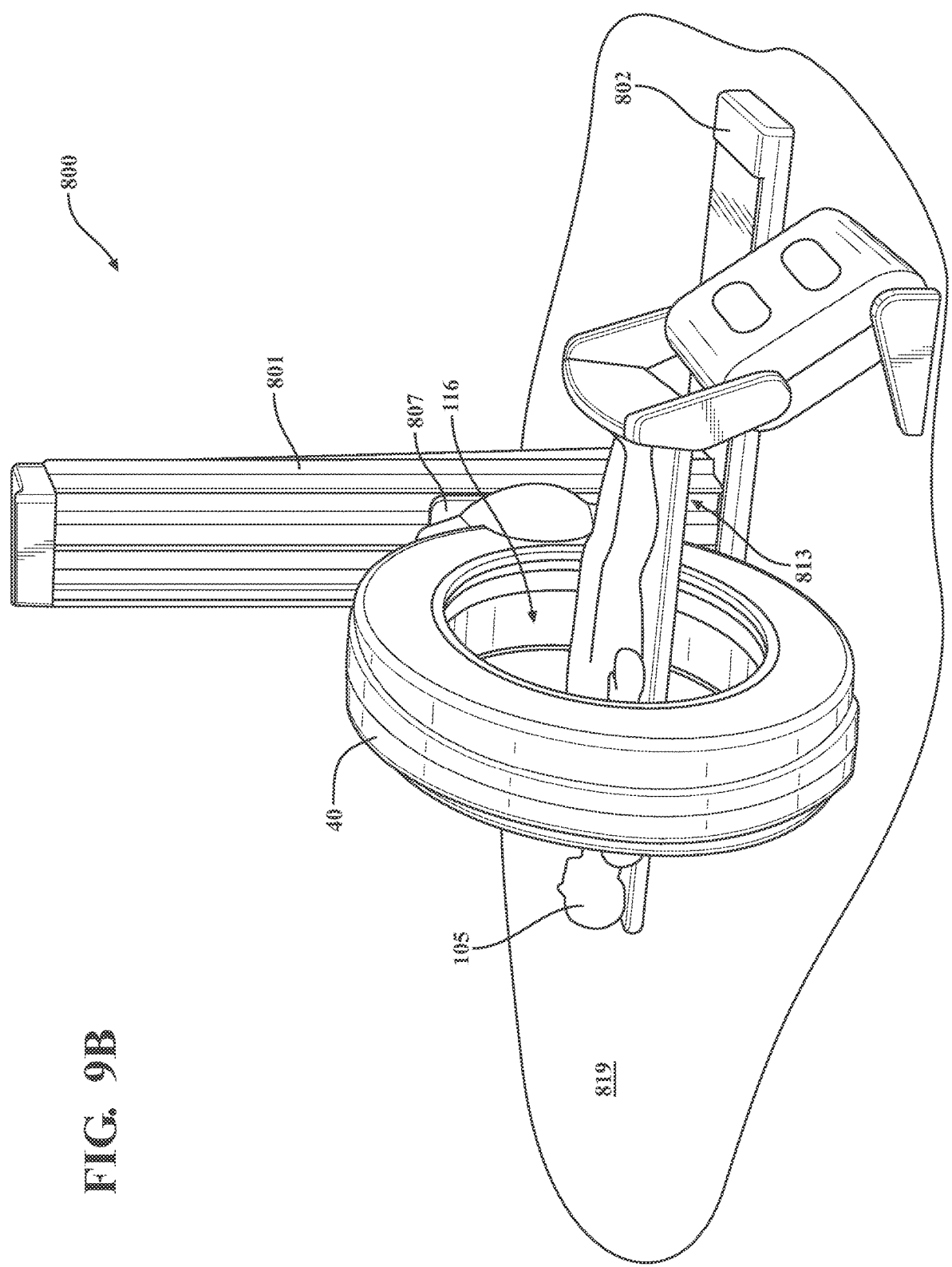
Figure 9C:
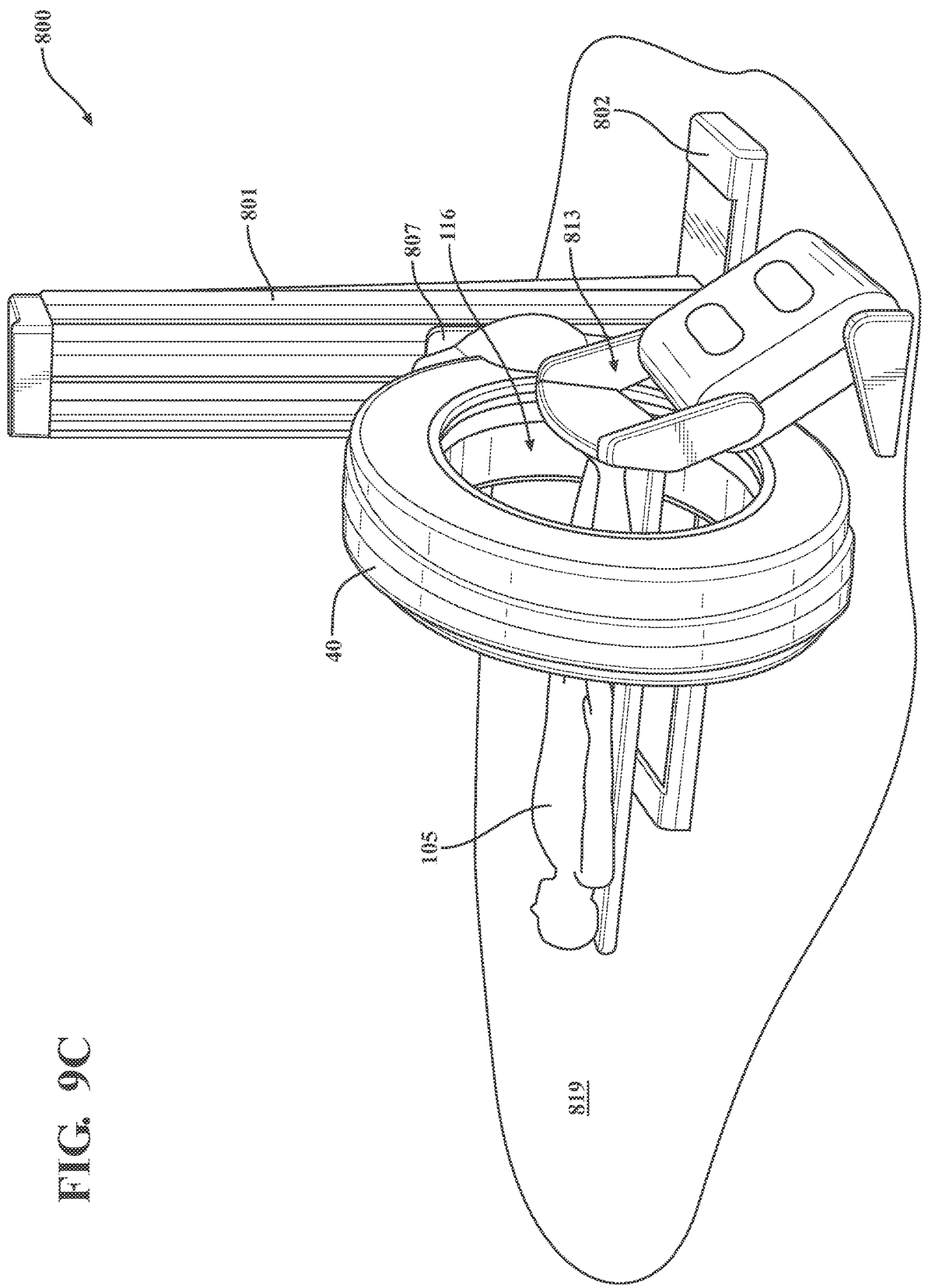

The gantry 40 may be attached to the support column 801 by the attachment mechanism 807 such that the gantry 40 may pivot (i.e., tilt) with respect to the support column 801. This is illustrated in FIGS. 9A-9C, which illustrate the gantry 40 pivoted from a generally vertical orientation (as shown in FIGS. 8A-8C) with the front and rear faces of the gantry 40 extending parallel to the floor 819 and the imaging axis 114 extending in a vertical direction (i.e., perpendicular to the floor) to a generally horizontal orientation with the front and rear faces of the gantry extending perpendicular to the floor 819 and the imaging axis 114 extending in a horizontal direction (i.e., parallel to the floor). The imaging axis 114 of the gantry 40 in the configuration shown in FIGS. 9A-9C may extend perpendicular to the length dimension of the vertically-extending support column 801.

In embodiments, the gantry 40 may be attached to the attachment mechanism 807 via a bearing assembly (i.e., a rotary bearing assembly) that allows the gantry 40 to pivot with respect to the support column 801. In one embodiment, the rotary bearing assembly may include a first portion (i.e., bearing race) mounted to the attachment mechanism 807 and a second portion (i.e., bearing race) mounted to the gantry 40. The two bearing portions may rotate concentrically relative to one another such that the gantry 40 may be rotated relative to the attachment mechanism 807 and support column 801. In embodiments, the gantry 40 may rotate at least about 90° relative to the support column 801 (e.g., as is illustrated by FIGS. 8A-8C and FIGS. 9A-9C).

In some embodiments, the patient support 813 may move from a first configuration as shown in FIGS. 8A-8C to a second configuration as shown in FIGS. 9A-9C. In the configuration of FIGS. 8A-8C, the first portion 815 of the patient support 813 may extend in a generally horizontal direction (i.e., parallel to the floor 819) and the second portion 817 may extend in a generally vertical direction (i.e., away from the floor 819). In the configuration of FIGS. 9A-9C, the second portion 817 of the patient support 813 may extend in a generally horizontal direction (i.e., parallel to the floor 819) and the first portion 815 may extend in a generally vertical direction. Put another way, the patient support 813 may tilt by a predetermined angle (e.g., ~90°) relative to the floor 819 between the configuration shown in FIGS. 8A-8C and the configuration shown in FIGS. 9A-9C. In embodiments, the table configuration of FIGS. 8A-8C may be used for scanning a patient in a weight-bearing standing position and the table configuration of FIGS. 9A-9C may be used for scanning a patient in a lying position.

In some embodiments, the patient support 813 may rotate (tilt) with respect to a linkage member 821 to which the patient support 813 is attached. In embodiments, the linkage member 821 may also rotate with respect to the floor 819. For example, the linkage member 821 may be attached to a base 823 that may be mounted to the floor 819. The linkage member 821 may rotate relative to the base 823. The rotation of the linkage member 821 relative to the base 823 may raise and lower the patient support 813 relative to the floor 819. A control system may provide coordinated rotational motion of the patient support 813 relative to the linkage member 821 and rotational motion of the linkage member 821 relative to the base 823 to move the table system from the configuration shown in FIGS. 8A-8C to the configuration shown in FIGS. 9A-9C. An example of a patient table system that may be used with the system 800 is described in U.S. Provisional Patent Application No. 62/380,595 filed on Aug. 29, 2016, the entire contents of which are incorporated by reference herein.

FIGS. 9A-9C illustrate the system 800 performing an imaging scan of a patient 105 in a lying position. In particular, for an x-ray CT imaging system, the x-ray source and detector may rotate within the gantry 40 around the patient 105 while the gantry 40 is translated relative to the patient support 813 in a generally horizontal direction to perform a helical scan of a patient 105 lying on the patient support 813. In the embodiment shown in FIGS. 9A-9C, the gantry 40, attachment mechanism 807 and support column 801 may translate relative to the patient 105 and patient support 813, which may be stationary during the scan. The gantry 40, attachment mechanism 807 and the support column 801 may translate along the length of the base 802. As shown in FIGS. 9A-9C, the gantry 40 may be displaced vertically on the support column 801 such that the patient 105 is aligned with the bore 116 of the gantry 40 and the imaging axis 114 extends along the length of the patient 105. The gantry 40, attachment mechanism 807 and the support column 801 may then translate along the base 802 in a horizontal direction from a first position as shown in FIG. 9A with the gantry 40 located over the head of the patient 105, to a second position as shown in FIG. 9B with the gantry 40 located over the mid-section of the patient 105, to a third position as shown in FIG. 9C with the gantry 40 located over the feet of the patient 105. The system 800 may perform a horizontal scan over the full length of the patient 105 or any selected portion thereof.

The base 802 and the support column 801 may include mating features that confine the translation of the support column in a horizontal direction along the length of the base 802. In the example of FIGS. 9A-9C, the base 802 may include a horizontal guide, such as rails or tracks, that may mate with corresponding features at the bottom of the support column 801 to guide the translation of the support column 801 in a horizontal direction. A second drive mechanism may drive the translation of the support column 801 relative to the base 802. A second drive mechanism 812 for translating the gantry 40 and support column 801 is schematically illustrated in FIG. 10A. The second drive mechanism may comprise, for example, a belt drive, a drive wheel, a lead screw, a ball screw, a pulley, etc. or various combinations therefore. The second drive mechanism may be mechanically coupled to and driven by one or more motors, which may be located in the support column 801 and/or the base 802. The controller 810 (see FIG. 10A) may control the operation of the second drive mechanism and thereby control the horizontal translation of the support column 801, attachment mechanism 807 and gantry 40. The controller may receive position feedback signals indicative of the position of the support column 801 relative to the base 802, such as from a linear encoder.

Figure 10B:
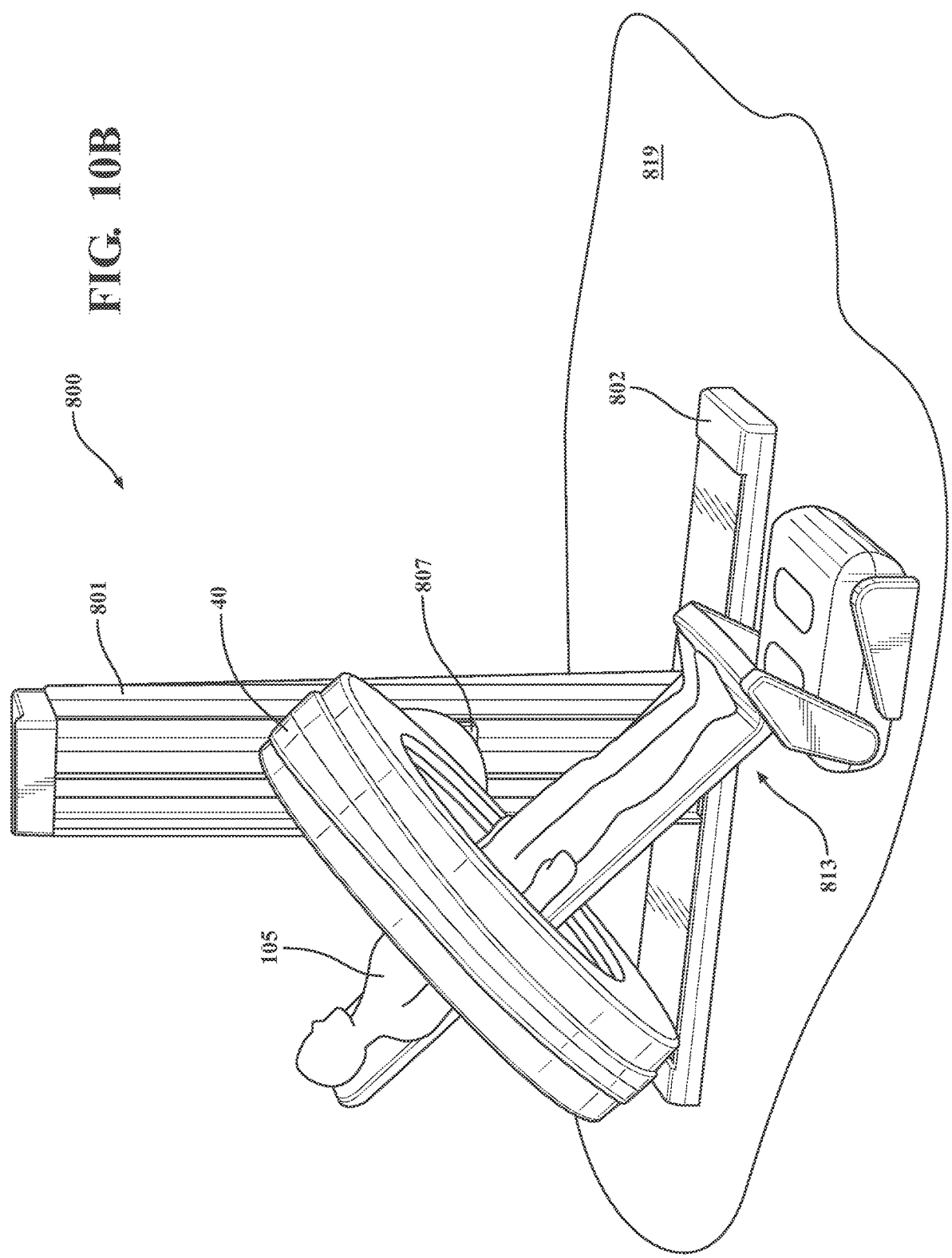

FIGS. 10A-10C illustrate the system 800 performing an imaging scan of a patient 105 along a tilted axis. The patient 105 may be supported by the patient support 813 at an oblique angle such that an axis 1014 extending lengthwise through the patient 105 is neither parallel or perpendicular to the floor 819. This may be achieved, for example, by rotating (tilting) the patient support 813 and patient 105 from a standing position (as shown in FIGS. 8A-8C) or rotating (tilting) the patient support 813 and patient 105 upwards from a lying position (as shown in FIGS. 9A-9C). The gantry 40 may be pivoted with respect to the support column 801 such that the imaging axis 114 through the bore 116 is parallel to, and optionally collinear with, the patient axis 1014. The system 800 may perform an imaging scan (e.g., a helical x-ray CT scan) of the patient 105 by moving the gantry 40 in the direction of the tilted patient axis 1014 while maintaining a fixed angle between the gantry 40 and axis 1014. In various embodiments, the controller 810 of the imaging system 800 may provide a coordinated movement of the gantry 40 and attachment mechanism 807 relative to the support column 801 in a vertical direction with a movement of the gantry 40, attachment mechanism 807 and support column 801 relative to the base 802 in a horizontal direction. The controller 810 may include logic configured to determine the relative vertical and horizontal displacement of the gantry 40 needed to move the gantry 40 along the tilted axis 1014. The controller 810 may send control signals to the first and second drive mechanisms 808, 812 as described above to provide coordinated vertical and horizontal displacement of the gantry 40. Where the angle of the tilted axis 1014 is known or may be determined, the controller 810 may use simple trigonometric relations to determine the vertical and horizontal displacement of the gantry 40. As in the embodiment of FIGS. 5A-5C, for example, where the tilted axis 1014 is at an angle of 60° relative to horizontal, each cm of the scan along the axis 1014 may include a vertical displacement of the gantry 40 relative to the support column 801 of ~0.87 cm (i.e., sin 60°) and a horizontal displacement of the gantry 40 and support column 801 relative to the base 802 of 0.5 cm (i.e., cos 50°). Thus, the imaging system 800 may perform a scan at any tilt axis 1014, and in embodiments may perform scans along complex axes, such as along an angled or curved axis.

FIGS. 10A-10C illustrate the system 800 performing an imaging scan of a patient 105 along a tilted axis 1014. In particular, for an x-ray CT imaging system, the x-ray source and detector may rotate within the gantry 40 around the patient 105 while the gantry 40 is displaced in both vertical and horizontal directions to perform a helical scan of the patient 105 along a tilted axis 1014. The patient may be supported on a patient support 813 that may be tilted such that the second portion 817 of the patient support 813 may extend parallel to the tilted axis 1014. The gantry 40 may be pivoted with respect to the support column 801 to align the gantry imaging axis 814 with the tilted axis 1014. The gantry 40 may be moved in both a vertical and horizontal direction from a first position as shown in FIG. 10A with the located over the head of the patient 105, to a second position as shown in FIG. 10B with the gantry 40 located over the mid-section of the patient 105, to a third position as shown in FIG. 10C with the gantry 40 located over the feet of the patient 105. The system 800 may perform scan over the full length of the patient 105 or any selected portion thereof.

Figure 11A:
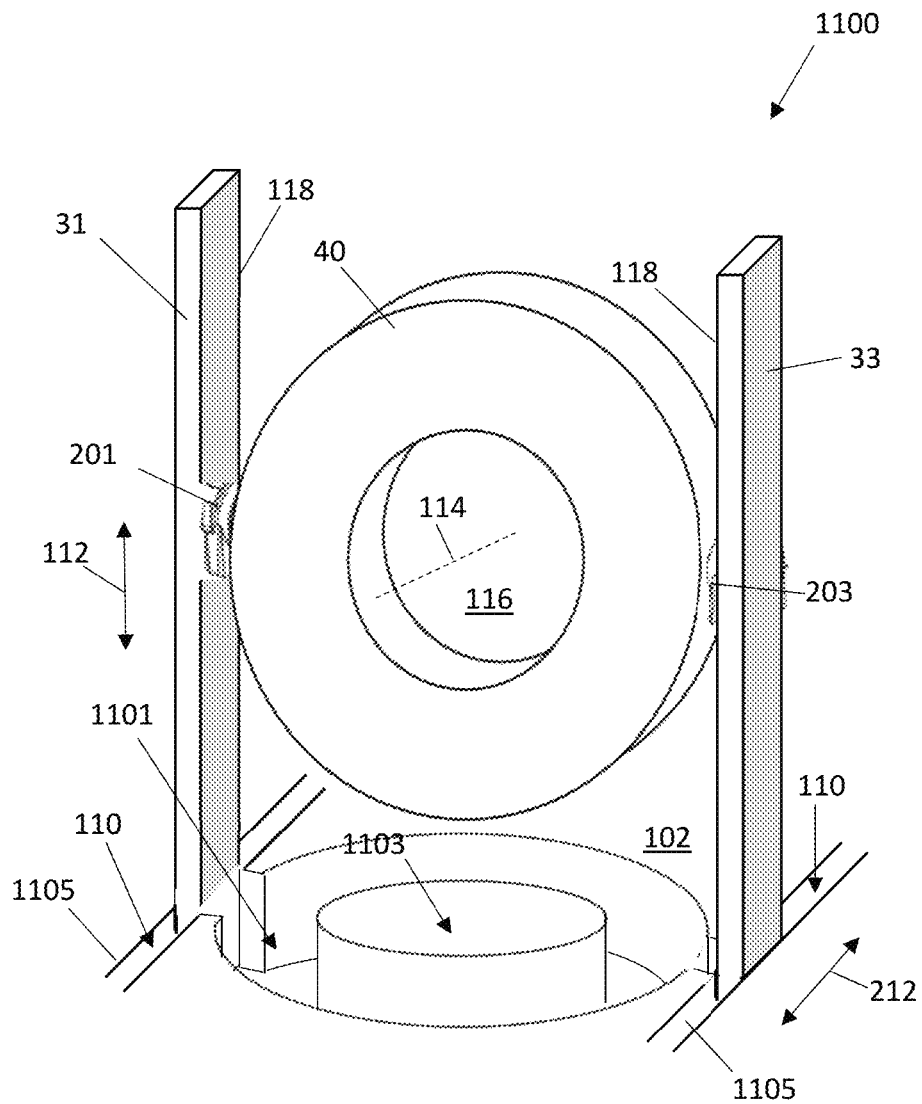
FIGS. 11A-11C illustrate an x-ray CT imaging system having an imaging gantry supported by a pair of support columns and a cavity in a base of the imaging system configured to receive the gantry.
Figure 11B:
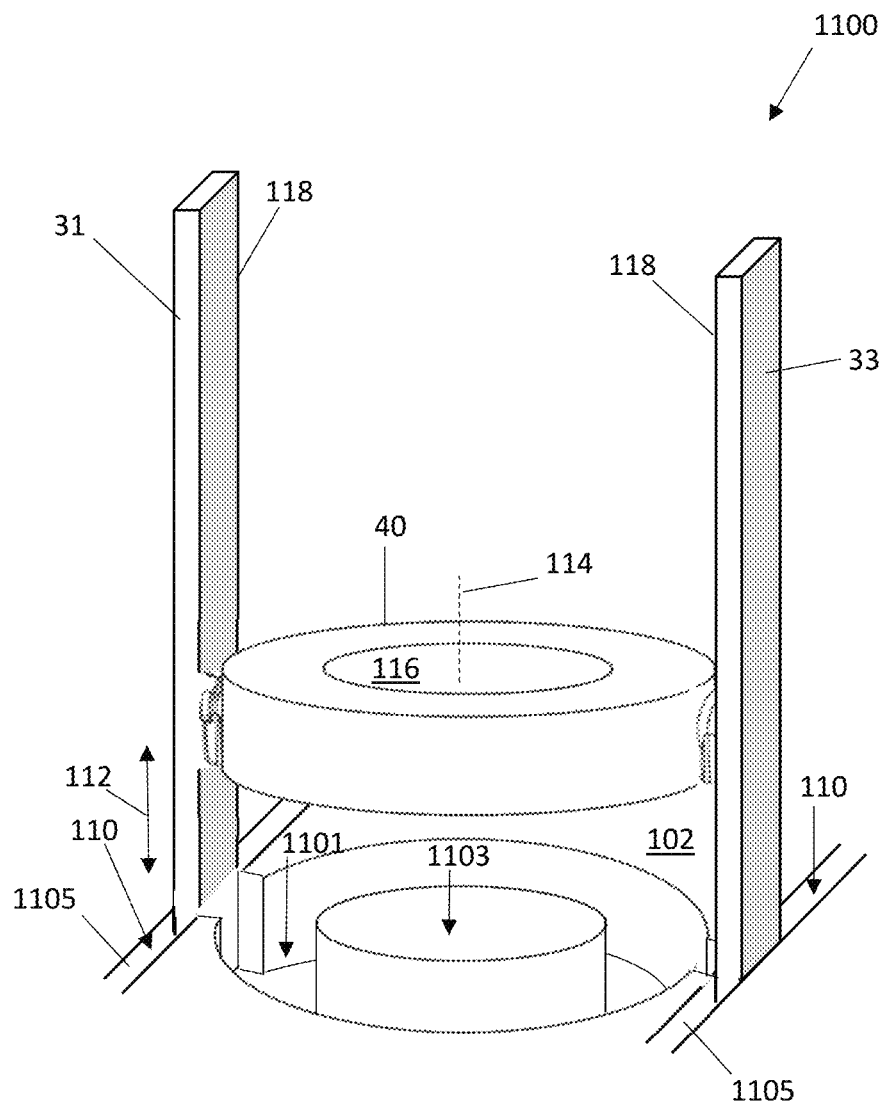
Figure 11C:
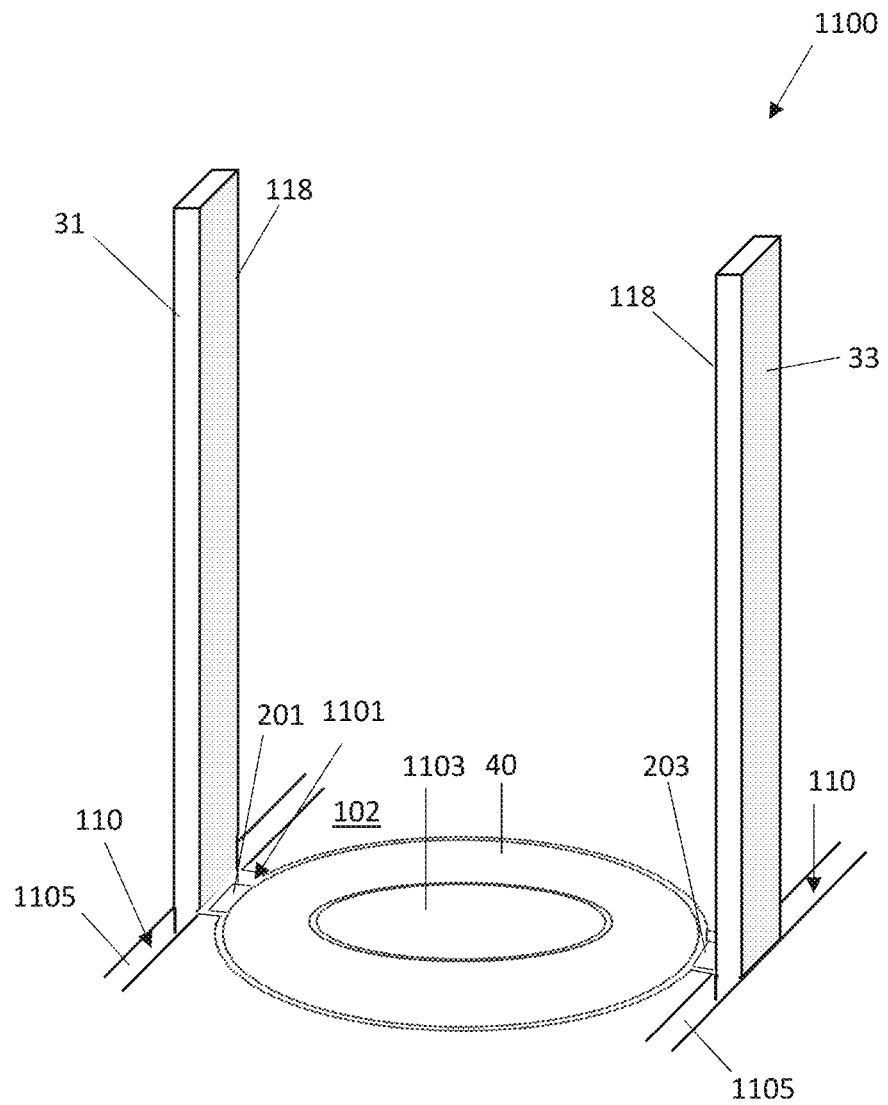

FIGS. 11A-11C illustrate yet another embodiment of an imaging system 1100. The imaging system 1100 in this embodiment is similar to the imaging system 100 described above with reference to FIGS. 1A-5C, and includes an imaging gantry 40 and a pair of support columns 31, 33 that extend vertically on opposite sides of the gantry 40. The pair of support columns 31, 33 may be attached to opposite sides of the gantry by a pair of attachment mechanisms 201, 203. The gantry 40 may be a generally O-shaped structure having a central imaging bore 116 and defining an imaging axis 114 extending through the bore. The imaging system 1100 may be an x-ray imaging system and the gantry 40 may contain one of more of the x-ray imaging components described above with reference to FIG. 6, such as an x-ray source, an x-ray detector, a high-voltage generator, a heat exchanger, a power supply (e.g., battery system), and a computer.

The imaging system 1100 further includes a base 102, and the support columns 31, 33 extend vertically above a top surface of the base 102. As shown in FIG. 11A, the gantry 40 is supported between the pair of support columns 31, 33 and above the top surface of the base 102. In the configuration shown by FIG. 11A, the support columns 31, 33 support the gantry with the imaging axis 114 in a horizontal orientation.

Attachment mechanism 201 mates with at least one vertical rail 118 on support column 31, and attachment mechanism 203 mates with at least one vertical rail 118 on support column 33. The pair of attachment mechanisms 201, 203 are moveable along the vertical rails 118 of the support columns 31, 33 to cause the pair of attachment mechanisms 201, 203 and the gantry 40 to which they are attached to move up and down along the support columns 31, 33 in the direction of arrow 112. A first drive mechanism (see 808 in FIG. 10A) may move the attachment mechanisms 201, 203 and gantry 40 along the support members 31, 33.

The support columns 31, 33, the attachment mechanisms 201, 203 and the gantry 40 are moveable with respect to the base 102. A second drive mechanism (see 812 in FIG. 10A) may move the support columns 31, 33, attachment mechanisms 201, 203 and gantry 40 back and forth along the base 102 in the direction of arrow 212. The second drive mechanism may move the gantry 40, attachment mechanisms 201, 203 and support columns 31, 33 in a horizontal direction along the base 102 in coordination with the rotation of x-ray imaging components around the bore 116 in order to perform a helical CT scan of a human or animal patient positioned within the bore 116 (e.g., on a patient table, not illustrated in FIG. 11A).

The base 102 may include a pair of horizontal guides 110, and each of the support columns 31, 32 may move along a respective horizontal guide 110. In the embodiment shown in FIGS. 11A-11C, the support columns 31, 33 may extend into the base 102, and the horizontal guides 110 may include a pair of parallel slots 1105 within which the support columns 31, 33 may move. The support columns 31, 33 may also engage with a one or more guide rails, such as shown in FIGS. 1A-5C, which may be located inside the slots 1105.

Each of the attachment mechanisms 201, 203 may attach to a side of the gantry 40 via a bearing assembly that allows the gantry 40 to pivot with respect to the support columns 31, 33. As shown in FIGS. 11A-11B, the gantry 40 may pivot from a configuration in which the pair of support columns 31, 33 support the gantry 40 with the imaging axis 114 in a horizontal orientation (see FIG. 11A) to a configuration in which the pair of support columns 31, 33 support the gantry 40 with the imaging axis 114 in a vertical orientation (see FIG. 11B). The gantry 40 may also be pivoted to a configuration in which the support columns 31, 33 support the gantry 40 with the imaging axis 114 of the gantry 40 orientated along a tilted axis that is neither vertical nor horizontal, such as shown in FIGS. 5A-5C and 10A-10C.

In embodiments, the first drive mechanism may move the pair of attachment mechanisms 201, 203 and the gantry 40 on the vertical rails 118 along the support columns 31, 33 while the support columns 31, 33 support the gantry 31 with the imaging axis 114 in a vertical orientation as shown in FIG. 11B in order to perform a vertical scan of a human or animal patient located within the bore 116 of the gantry 40. The patient may be scanned in a weight-bearing (e.g., standing) position. The attachment mechanisms 201, 203 and the gantry 40 may move vertically along the support columns 31, 33 in coordination with the rotation of x-ray imaging components around the bore 116 in order to perform a helical CT scan of the patient.

In addition, while the support columns 31, 33 support the gantry 40 with the imaging axis 114 orientated along a tilted axis, a controller (see 810 in FIG. 10A) may control the first and second drive mechanisms to move the gantry 40 in both vertical and horizontal directions in a coordinated manner in order to perform an x-ray imaging scan along the tilted axis, as described above with reference to FIGS. 5A-5C and 10A-10C.

As shown in FIGS. 11A-11C, the base 102 of the imaging system 1100 may also include a cavity 1101 configured to receive the gantry 40 so that the gantry 40 is housed within the base 102. The cavity 1101 may have a size and shape that corresponds to the size and shape of the gantry 40 while the support columns 31, 33 support the gantry 40 with the imaging axis 114 in a vertical orientation. The cavity 1101 may also be sized and shaped to accommodate the attachment mechanisms 201, 202, as shown in FIGS. 11A-11C.

In the embodiment of FIGS. 11A-11C, the gantry 40 may be pivoted to a configuration in which the pair of support columns 31, 33 support the gantry 40 with the imaging axis 114 in a vertical orientation, as shown FIG. 11B. Optionally, the support columns 31, 33, attachment mechanisms 201, 203 and gantry 40 may be moved along the base 102 on the horizontal guides 110 to position the gantry in alignment with the cavity 1101 in the base 102. The first drive mechanism may move the gantry 40 and attachment mechanisms 201, 203 down along the vertical rails 118 of the support members 31, 33 to move the gantry 40 and attachment mechanisms 201, 203 into the cavity 1101 in the base 102.

The cavity 1101 may have a depth that is at least as large as the width dimension of the gantry 40 so that the gantry 40 may fully enter the cavity 1101. This may enable the gantry 40 to be moved completely out of the way and safely stored in the cavity 1101 when not in use. In the embodiment shown in FIG. 11C, the gantry 40 is moved into the cavity 1101 so that the outer surface of the gantry 40 is level with the top surface of the base 102. In some embodiments, a door or similar cover (not illustrated in FIG. 11C) may optionally be moved into place over the top of the cavity 1101 to fully enclose the gantry 40 within the cavity 1101. As shown in FIG. 11C, the shape of the cavity 1101 may roughly correspond to both the outer and inner dimensions of the gantry 40 so that a portion 1103 of the base 102 interior of the cavity 1101 may fill the space within the bore 116 of the gantry 40 when the gantry 40 is located inside of the cavity 1101.

When the imaging system 1100 is needed to perform an imaging scan, the first drive mechanism may move the gantry 40 and attachment mechanisms 201, 203 up along the vertical rails 118 of the support columns 31, 33 to move the gantry 40 and attachment mechanisms 201, 203 out of the cavity 1101. The attachment mechanisms 201, 203 and the gantry 40 may move vertically along the support columns 31, 33 in coordination with the rotation of x-ray imaging components around the bore 116 in order to perform a vertical imaging scan (e.g., a helical x-ray CT scan) of a patient in a weight-bearing position. The patient may stand on the portion 1103 of the base 102 interior of the cavity 1101 during the imaging scan. Alternately, the gantry 40 and attachment mechanisms 201, 203 may be raised out of the cavity 1101, and the second drive mechanism may move the support columns 31, 33 along the horizontal guides 110 of the base 102 in order to move the gantry 40, attachment mechanisms 201, 203 and support columns 31, 33 away from the cavity 1101 to a different portion of the base 102 in order to perform a vertical imaging scan. To perform an imaging scan in a horizontal direction or along a titled axis, the gantry 40 may be pivoted to a configuration in which the support columns 31, 33 support the gantry 40 with the imaging axis oriented in a horizontal direction or along a tilted axis that is neither vertical nor horizontal. The second drive mechanism may move the gantry 40, attachment mechanisms 201, 203 and support columns 31, 33 in a horizontal direction along the base 102 in coordination with the rotation of x-ray imaging components around the bore 116 in order to perform a helical CT scan of a human or animal patient positioned within the bore 116.

Although the imaging system 1100 shown in FIGS. 11A-11C includes a pair of support columns 31, 33 attached to opposite sides of the gantry 40, it will be understood that alternative embodiments may include a single support column 801 that is mounted to a first side of the gantry 40 by an attachment mechanism 807 and that supports the gantry 40 in a cantilevered manner, such as shown in FIGS. 8A-10C. In addition, although the embodiment shown in FIGS. 11A-11C includes a cavity 1101 for housing the gantry 102 located within the base 102 of the imaging system 1100, it will be understood that in alternative embodiments, the cavity 1101 may be located in the floor.

FIGS. 12A-12D illustrate an alternative embodiment of an imaging system 1200 having a single support column supporting the imaging gantry and a cavity in the floor that is configured to receive the gantry. The imaging system 1200 in this embodiment may be similar to the imaging system 800 described above with reference to FIGS. 8A-10C, and includes a base 802, a support column 801 located on and supported by the base 802, and a gantry 40 supported by the support column 801 in a cantilevered manner. An attachment mechanism 807 may be attached to one side of the gantry 40, and may be located between the side of the gantry 40 and the support column 801. The attachment mechanism 807 may engage with vertical rails 805, 806 extending along the support column 801 that enable the gantry 40 and attachment mechanism 807 to move up and down along the support column 801.

The floor surface may include a first portion 1201 and a second portion 1204, where the first portion 1201 may be raised relative to the second portion 1204. The base 802 of the imaging system 1200 may be located on the second portion 1204, so that it is recessed relative to the first portion 1201. In the embodiment of FIGS. 12A-12D, the raised portion 1201 is the upper surface of a platform. A ramp 1202 may extend between the raised portion 1201 and the second portion 1204 of the floor surface.

Figure 12A:
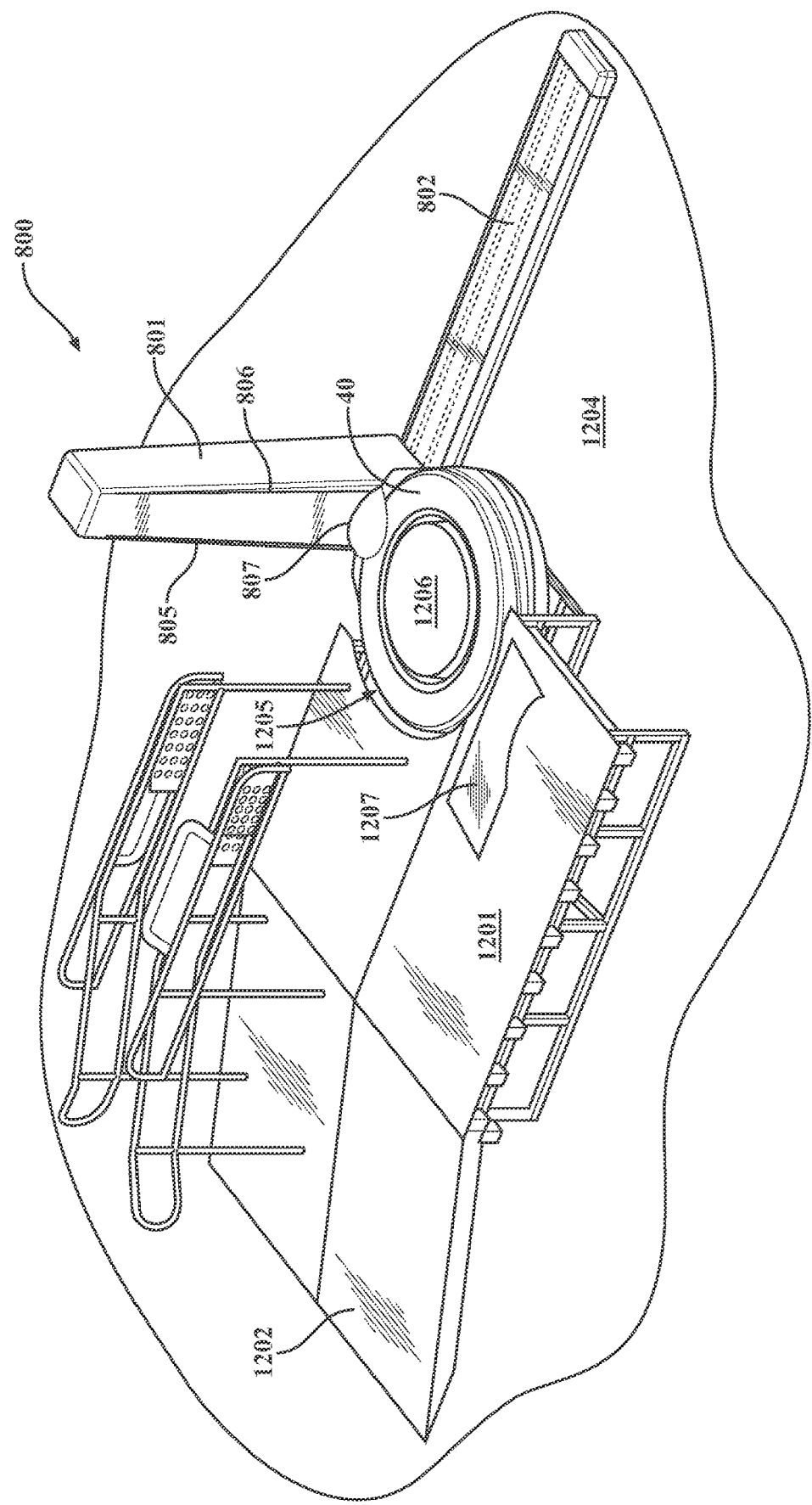
FIGS. 12A-12D illustrate an x-ray CT imaging system having an imaging gantry supported by a support column and a cavity in the floor configured to receive the gantry.

As shown in FIGS. 12A-12D, the first portion 1201 of the floor surface includes a cavity 1205 configured to receive the gantry 40. The cavity 1205 may have a size and shape that corresponds to the size and shape of the gantry 40. FIG. 12A shows the gantry 40 located within the cavity 1205. In the embodiment shown in FIG. 12A, the outer surface of the gantry 40 is level with the first portion 1201 of the floor surface. A section 1206 of the first portion 1201 of the floor surface that is interior of the cavity 1205 has a size and shape that corresponds to the size and shape of the bore 116 of the gantry 40. This section 1206 fills the space within the bore 116 when the gantry 40 is in the cavity 1205, as shown in FIG. 12A. In this embodiment, the cavity 1205 is located at a corner of the first portion 1201 of the floor surface, so that the first portion 1201 extends around a portion of the outer circumference of the gantry 40. FIG. 12A also illustrates a door 1207 that may be pivotably mounted to the first portion 1201 of the floor surface so that the door 1207 may be pivoted over the top of the cavity 1205 and cover at least a portion of the gantry 40.

Figure 12B:
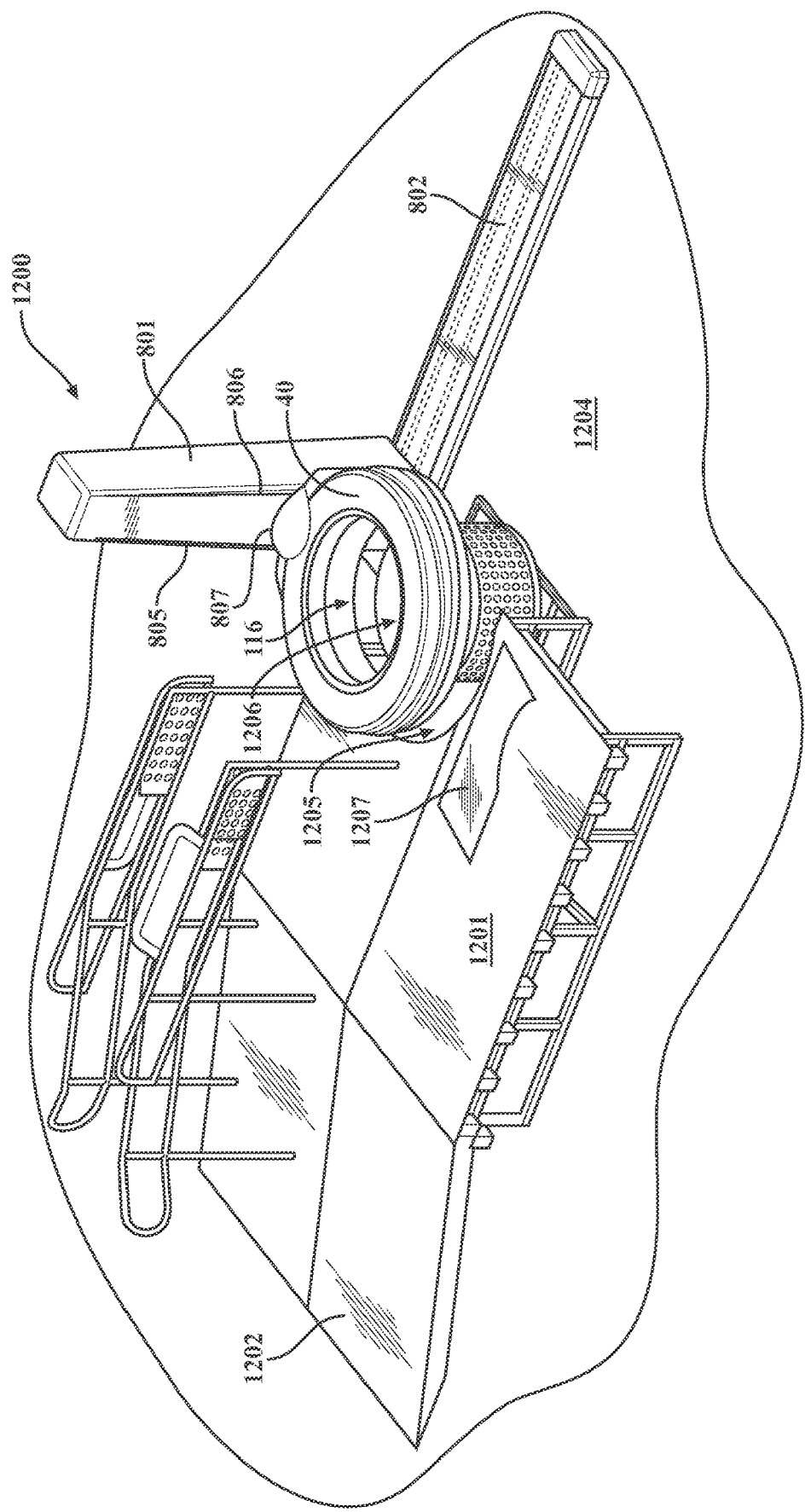
Figure 12C:
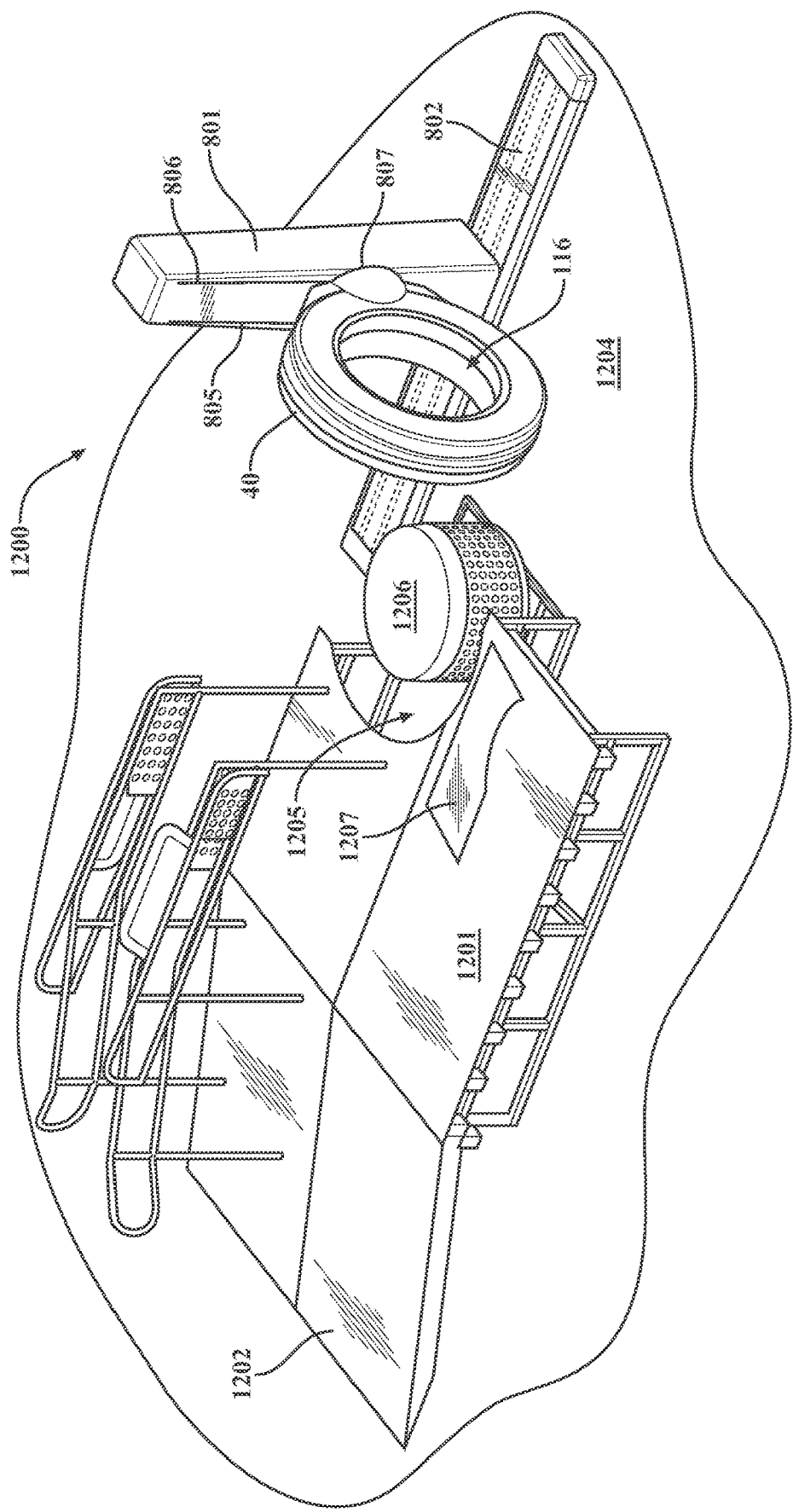
Figure 12D:
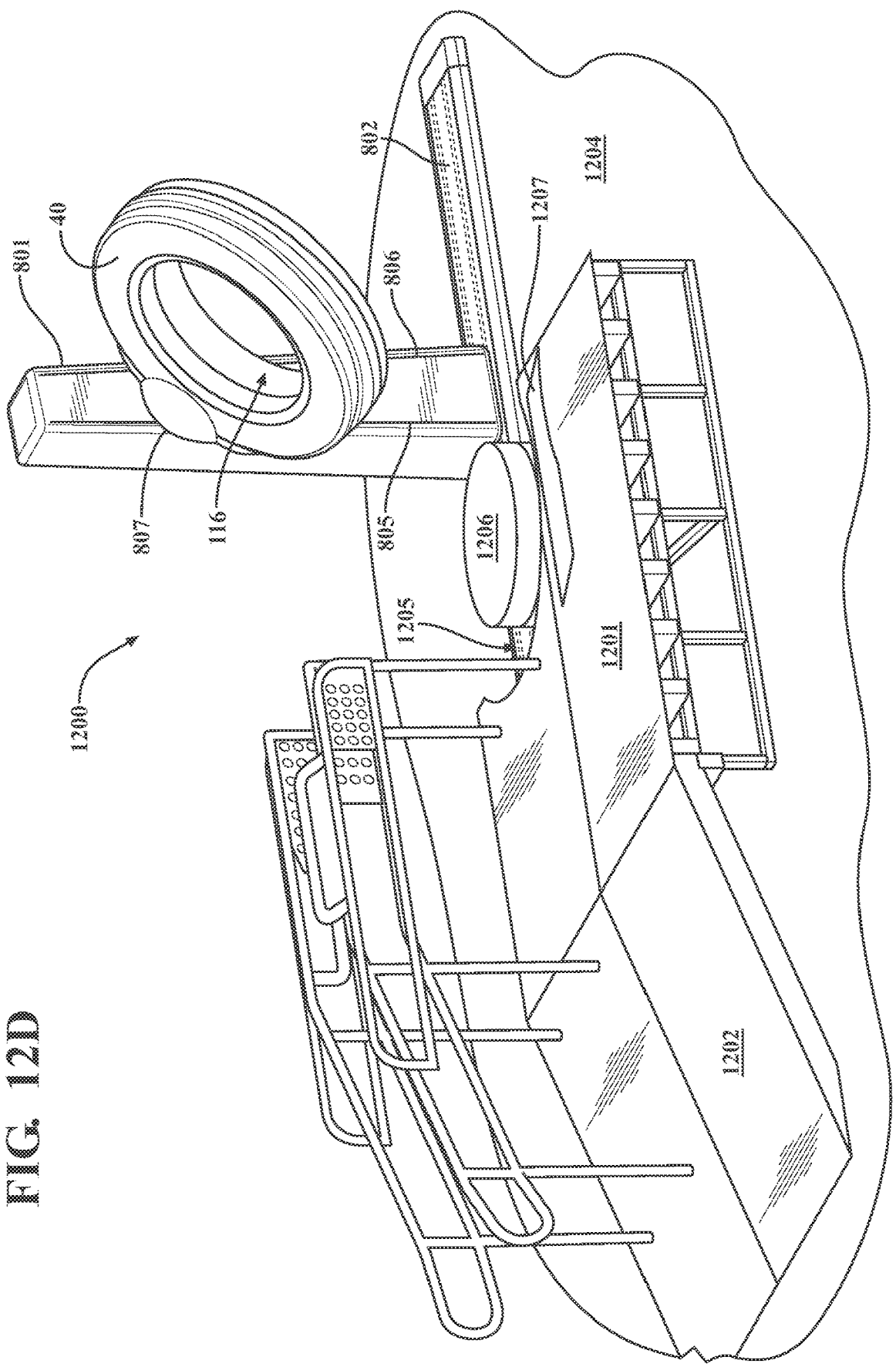

When the imaging system 1200 is needed to perform an imaging scan, a first drive mechanism (see FIG. 10A) may move the gantry 40 and the attachment mechanism 807 up along the vertical rails 805, 806 of the support column 801 to move the gantry 40 and attachment mechanism 807 out of the cavity 1205, as shown in FIG. 12B. The gantry 40 and attachment mechanism 807 may move vertically along the support column 801 in coordination with the rotation of x-ray imaging components around the bore 116 in order to perform a vertical imaging scan (e.g., a helical x-ray CT scan) of a patient in a weight-bearing position. The patient may stand on the section 1206 of the floor surface 1201 interior of the cavity 1205 during the imaging scan. Alternately, the gantry 40 and attachment mechanism 807 may be raised out of the cavity 1205, and a second drive mechanism may move the support column 801 along the length of the base 802 in order to move the gantry 40, and attachment mechanism 807 away from the cavity 1205 to a different location for performing a vertical imaging scan. To perform an imaging scan in a horizontal direction or along a titled axis, the gantry 40 may be pivoted on a bearing assembly between the attachment mechanism 807 and the gantry 40 to a configuration in which the support column 801 supports the gantry 40 with the imaging axis oriented in a horizontal direction (as shown in FIG. 12C) or along a tilted axis that is neither vertical nor horizontal (as shown in FIG. 12D). The second drive mechanism may move the gantry 40, attachment mechanism 807 and support column 801 in a horizontal direction along the base 802 in coordination with the rotation of x-ray imaging components around the bore 116 in order to perform a helical CT scan of a human or animal patient positioned within the bore 116.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

TABLE

| Reference Number | Component Represented |
|---|---|
| 31 | Support column |
| 33 | Support column |
| 35 | Docking system |
| 40 | Gantry |
| 41 | Rotor |
| 42 | Outer shell of gantry |
| 43 | X-ray source |
| 44 | High-voltage generator |
| 45 | X-ray detector |
| 46 | Computer |
| 47 | Rotor drive mechanism |
| 50 | Table Column |
| 60 | Tabletop support |
| 63 | Power supply |
| 100 | Imaging system |
| 101 | Rotating portion of imaging system |
| 102 | Base |
| 105 | Patient |
| 110 | Horizontal guide on base |
| 112 | Arrow indicating direction of displacement of gantry |
| 114 | Imaging axis |
| 116 | Bore |
| 118 | Vertical rail on support column |
| 201 | Attachment mechanism for attaching gantry to support member |
| 202 | Support structure |
| 203 | Attachment mechanism for attaching gantry to support member |
| 212 | Arrow indicating direction of relative displacement of gantry and tabletop support |
| 400 | Bearing assembly |
| 402 | First race of bearing assembly |
| 404 | Second race of bearing assembly |
| 406 | Outer circumferential surface of outer shell of gantry |
| 412 | Side wall of outer shell of gantry |
| 430 | Heat exchanger |
| 514 | Tilted axis |
| 800 | Imaging system |
| 801 | Support column |
| 802 | Base |
| 805, 806 | Vertical rails |
| 807 | Attachment mechanism for attaching gantry to support column |
| 808 | First drive mechanism that moves the attachment mechanism and the gantry along the support column |
| 809 | Interior housing of support column |
| 810 | Controller |
| 811 | Opening along length of support column |
| 812 | Second drive mechanism that moves the support column, attachment mechanism and gantry along the base |
| 813 | Patient support |
| 815 | First portion of patient support |

TABLE-continued

| Reference Number | Component Represented |
|---|---|
| 817 | Second portion of patient support |
| 819 | Floor |
| 821 | Linkage member attached to patient support |
| 823 | Base mounted to floor and attached to linkage member |
| 1014 | Axis extending lengthwise through patient |
| 1100 | Imaging system |
| 1105 | Parallel slots in base |
| 1101 | Cavity in the base |
| 1103 | Portion of the base interior of the cavity |
| 1200 | Imaging system |
| 1201 | First portion of floor surface that is raised relative to a second portion |
| 1202 | Ramp |
| 1204 | Second portion of floor surface that is recessed relative to the first portion |
| 1205 | Cavity configured to receive the gantry |
| 1206 | Section of floor surface interior of the cavity |
| 1207 | Door |

What is claimed is:

1. A method of imaging a human or animal patient using a multi-directional x-ray imaging system comprising a gantry having a central imaging bore and that contains an x-ray source component and an x-ray detector component that are configured for obtaining x-ray images of the human or animal patient positioned within the central imaging bore of the gantry, the gantry also including a housing and an internal cavity and the x-ray source component and the x-ray detector component are located within the housing and are rotatable around the housing within the internal cavity without the x-ray source component and the x-ray detector component entering into the central imaging bore of the gantry, and the gantry is mounted to a support column extending above a top surface of the base by an attachment mechanism that is attached to a side of the gantry and mates with at least one vertical rail extending vertically along the support column, the method comprising:
   moving the gantry in a horizontal direction by moving the support column, attachment mechanism and gantry forward or backwards along a horizontal guide in the base;
   obtaining x-ray image data of the human or animal patient using the x-ray source component and the x-ray detector component while the gantry is moved in a horizontal direction;
   rotating the gantry with respect to the support column into a vertical orientation with an imaging axis through the central imaging bore extending vertically using a bearing assembly located between the gantry and the attachment mechanism; and
   lowering the gantry into a cavity in the base or floor by moving the attachment mechanism and the gantry on the at least one vertical rail in a downward direction along the support column while the gantry is in the vertical orientation.

2. The method of claim 1, further comprising:
   raising the gantry out of the cavity in the base or floor by moving the attachment mechanism and the gantry along the one or more vertical rails in an upward direction along the support column; and
   while the gantry is in the vertical orientation, obtaining x-ray image data of a human or animal patient positioned within the central imaging bore using the x-ray source component and the x-ray detector component by moving the attachment mechanism and the gantry on the at least one vertical rail up or down along the support column.

3. The method of claim 2, further comprising:
   rotating the gantry with respect to the support column from the vertical orientation to a second orientation in which the imaging axis through the central imaging bore extends horizontally or along a tilted axis that is neither vertical nor horizontal using the bearing assembly located between the gantry and the attachment mechanism;
   moving the gantry in a horizontal direction by moving the support column, attachment mechanism and gantry forward or backwards along the horizontal guide in the base; and
   obtaining x-ray image data of a human or animal patient using the x-ray source component and the x-ray detector component while the gantry is moved in a horizontal direction.

4. The method of claim 1, wherein the cavity is in the base of the x-ray imaging system.

5. The method of claim 1, wherein the cavity is in the floor.

6. The method of claim 1, wherein gantry is mounted to a first support column extending above a top surface of the base by a first attachment mechanism that is attached to a first side of the gantry, and the gantry is also mounted to a second support column extending above the top surface of the base by a second attachment mechanism that is attached to a second side of the gantry that is opposite the first side of the gantry, the second attachment mechanism mating with at least one vertical rail extending vertically along the second support column, and wherein:
   moving the gantry in a horizontal direction comprises moving the first and second support columns, the first and second attachment mechanisms and the gantry forward or backwards along a pair of horizontal guides in the base;
   rotating the gantry into a vertical orientation comprises rotating the gantry with respect to the first and second support columns using a pair of bearing assemblies located between the first and second sides of the gantry and the first and second attachment mechanisms; and
   lowering the gantry into a cavity in the base or floor comprises moving the first and second attachment mechanisms and the gantry on the vertical rails in a downward direction along the first and second support columns.

7. A multi-directional x-ray imaging system, comprising:
   a gantry defining a central imaging bore and an imaging axis extending through the central imaging bore, with the gantry also having a housing and an internal cavity;
   an x-ray source component and an x-ray detector component that are configured for obtaining x-ray images of a human or animal patient located within the central imaging bore of the x-ray imaging system, where the x-ray source component and the x-ray detector component are located within the housing of the gantry and are rotatable around the housing of the gantry, within the internal cavity, without the x-ray source component and the x-ray detector component entering into the central imaging bore;
   a pair of support columns located on opposite sides of the gantry and supporting the gantry, with each of the support columns having at least one vertical rail that extends vertically along the support column;

a pair of attachment mechanisms, each attachment mechanism located between a side of the gantry and a support column and mating with the at least one vertical rail of the support column so that the attachment mechanism and the gantry are movable on the at least one vertical rail up and down along the support column, each of the attachment mechanisms also attaching to a side of the gantry via a bearing assembly to allow the gantry to pivot with respect to the pair of support columns between a first configuration in which the pair of support columns support the gantry with the imaging axis in a vertical orientation, and a second configuration in which the pair of support columns support the gantry with the imaging axis in a horizontal orientation;

a base having a pair of horizontal guides that extend horizontally along the base, the pair of support columns extending in a vertical direction above a top surface of the base, and the pair of support columns, the pair of attachment mechanisms and the gantry are moveable on the pair of horizontal guides back and forth along the base;

a first drive mechanism that moves the pair of attachment mechanisms and the gantry on the vertical rails up and down along the pair of support columns;

a second drive mechanism that moves the pair of support columns, the pair of attachment mechanisms and the gantry using the pair of horizontal guides back and forth along the base; and a cavity in the base or the floor that is configured to receive the gantry within the cavity while the pair of support columns support the gantry with the imaging axis in a vertical orientation.

8. The multi-directional x-ray imaging system of claim 7, wherein the cavity is in the base.

9. The multi-directional x-ray imaging system of claim 8, wherein the cavity is in the floor.

10. A multi-directional x-ray imaging system, comprising:

a gantry defining a central imaging bore and an imaging axis extending through the central imaging bore, with the gantry also having a housing, and an internal cavity;

an x-ray source component and an x-ray detector component that are configured for obtaining x-ray images of a human or animal patient located within the central imaging bore of the x-ray imaging system, where the x-ray source component and the x-ray detector component are located within the housing of the gantry and are rotatable around the housing of the gantry, within the internal cavity, without the x-ray source component and the x-ray detector component entering into the central imaging bore;

a support column supporting the gantry, with the support column having at least one vertical rail that extends vertically along the support column;

an attachment mechanism located between one side of the gantry and the support column, the attachment mechanism mating with the at least one vertical rail of the support column so that the attachment mechanism and the gantry are moveable on the at least one vertical rail up and down along the support column, the attachment mechanism also attaching to one side of the gantry via a bearing assembly that allows the gantry to pivot with respect to the support column between a first configuration in which the support column supports the gantry with the imaging axis in a vertical orientation, and a second configuration in which the support column supports the gantry with the imaging axis in a horizontal orientation;

a base having a horizontal guide that extends horizontally along the base, the single support column extending in a vertical direction above a top surface of the base and the support column, attachment mechanism and gantry are movable on the horizontal guide back and forth along the base, a first drive mechanism that moves the attachment mechanism and the gantry on the at least one vertical rail up and down along the support column;

a second drive mechanism that moves the support column, attachment mechanism and gantry using the horizontal guide back and forth along the base; and a cavity in the base or the floor that is configured to receive the gantry within the cavity while the support column supports the gantry with the imaging axis in a vertical orientation.

11. The multi-directional x-ray imaging system of claim 10, wherein the cavity is in the base.

12. The multi-directional x-ray imaging system of claim 10, wherein the cavity is in the floor.

* * * * *